US008428717B2

(12) United States Patent
Wang et al.

(10) Patent No.: US 8,428,717 B2
(45) Date of Patent: Apr. 23, 2013

(54) METHOD AND APPARATUS FOR MONITORING TISSUE FLUID CONTENT FOR USE IN AN IMPLANTABLE CARDIAC DEVICE

(75) Inventors: Li Wang, White Bear Township, MN (US); Yong K. Cho, Maple Grove, MN (US); Kevin Kuehn, Shoreview, MN (US); Glenn C. Zillmer, Hudson, WI (US); Nirav V. Sheth, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1039 days.

(21) Appl. No.: 10/684,759

(22) Filed: Oct. 14, 2003

(65) Prior Publication Data

US 2005/0080460 A1   Apr. 14, 2005

(51) Int. Cl.
*A61N 1/365* (2006.01)

(52) U.S. Cl.
USPC .......................................................... 607/17

(58) Field of Classification Search ...................... 607/17
See application file for complete search history.

(56) References Cited

U.S. PATENT DOCUMENTS

| 4,596,251 | A |   | 6/1986  | Plicchi et al. |
|-----------|---|---|---------|----------------|
| 4,901,725 | A |   | 2/1990  | Nappholz et al. |
| 5,117,824 | A |   | 6/1992  | Keimel et al. |
| 5,562,711 | A |   | 10/1996 | Yerich et al. |
| 5,562,712 | A |   | 10/1996 | Steinhaus et al. |
| 5,755,742 | A | * | 5/1998  | Schuelke et al. ............ 607/27 |
| 5,876,353 | A |   | 3/1999  | Riff |
| 5,957,861 | A | * | 9/1999  | Combs et al. ............ 600/547 |
| 5,987,352 | A |   | 11/1999 | Klein |
| 6,082,367 | A |   | 7/2000  | Greeninger et al. |
| 6,104,949 | A |   | 8/2000  | Pitts Crick et al. |
| 6,317,628 | B1 |  | 11/2001 | Linder et al. |
| 6,360,123 | B1 | * | 3/2002 | Kimchi et al. ............ 600/547 |
| 6,449,509 | B1 |  | 9/2002  | Park et al. |
| 6,473,640 | B1 |  | 10/2002 | Erlebacher |

(Continued)

FOREIGN PATENT DOCUMENTS

| DE | 10148440 A | 4/2003 |
| EP | 1384433 A | 1/2004 |
| WO | WO2005037367 A2 | 4/2005 |

OTHER PUBLICATIONS

Merriam-Webster Online Dictionary, www.webster.com, defined: metric.*

*Primary Examiner* — Niketa Patel
*Assistant Examiner* — Alyssa M Alter
(74) *Attorney, Agent, or Firm* — Reed A. Duthler; Stephen W. Bauer

(57) ABSTRACT

A fluid status monitoring system for use in implantable cardiac stimulation or monitoring devices is provided for monitoring changes in thoracic fluid content. A fluid status monitor includes excitation pulse generating and control circuitry, and voltage and current measurement and control circuitry for performing a series of cardiac-gated, intra-thoracic impedance measurements. The cardiac-gated measurements are filtered or time-averaged to provide a fluid status impedance value, with respiratory noise removed. Based on comparative analysis of the fluid status impedance value, a clinically relevant trend in fluid status may be tentatively diagnosed and a fluid status response provided. Cross-check intra-thoracic impedance measurements performed using the same or a different excitation pathway and a different measurement pathway than the primary intra-thoracic impedance measurement configuration may be used to verify a tentative diagnosis.

15 Claims, 15 Drawing Sheets

U.S. PATENT DOCUMENTS

| | | |
|---|---|---|
| 6,512,949 B1 | 1/2003 | Combs et al. |
| 2003/0023184 A1 | 1/2003 | Pitts Crick et al. |
| 2003/0028221 A1 | 2/2003 | Zhu et al. |
| 2003/0191503 A1 | 10/2003 | Zhu et al. |
| 2003/0220578 A1* | 11/2003 | Ho et al. ............ 600/521 |
| 2004/0172080 A1* | 9/2004 | Stadler et al. ............ 607/17 |

* cited by examiner

METHOD AND APPARATUS FOR MONITORING TISSUE FLUID CONTENT FOR USE IN AN IMPLANTABLE CARDIAC DEVICE

FIELD OF THE INVENTION

The present invention relates generally to the field of implantable cardiac stimulation devices and, more particularly, to a method and apparatus for monitoring changes in thoracic fluid content for use in implantable cardiac stimulation devices.

BACKGROUND OF THE INVENTION

A large percentage of patients having implantable cardioverter defibrillators also suffer from congestive heart failure (CHF). Increased fluid retention, a compensatory mechanism for increasing the cardiac output of the failing heart, eventually produces high venous pressure leading to pulmonary congestion (or edema) and respiratory dysfunction. Central to the treatment of CHF symptoms, therefore, is the management of a patient's fluid retention status, typically through the use of diuretics. However, patients can become over-diuresed which can cause added stress to the heart condition. Therefore, a careful balance of the patient's fluid status is important in managing the heart failure patient.

Pulmonary congestion/edema and CHF related respiratory disorders are common reasons for hospitalization of CHF patients. Hospitalizations could be reduced with improved monitoring of CHF symptoms such that early warning signs of a deteriorating CHF condition could be recognized and treated proactively. One method proposed for monitoring CHF in ambulatory patients is to measure intra-thoracic impedance to detect pulmonary congestion/edema. Preliminary studies show that measurements of intra-thoracic impedance can be good predictors of impending CHF-related hospitalization.

In U.S. Pat. No. 6,512,949 issued to Combs et al., an impedance monitor for discerning edema through evaluation of respiratory rate is generally disclosed. In U.S. patent application No. 2003/0028221 to Zhu et al., a cardiac rhythm management system having an edema detection circuit that includes a thoracic impedance circuit is generally disclosed. An implantable device for long term monitoring of CHF that includes measurement of systemic venous and pulmonary impedance is generally disclosed in U.S. Pat. No. 6,473,640 issued to Erlebacher.

The use of intra-thoracic impedance measurements for determination of minute ventilation has been implemented in implantable rate-responsive pacemakers. See, for example, U.S. Pat. No. 4,901,725 issued to Nappholz et al., U.S. Pat. No. 4,596,251 issued to Plicchi et al., U.S. Pat. No. 5,562,712 issued to Steinhaus et al., or U.S. Pat. No. 5,562,711 issued to Yerich et al. Methods for measuring intra-thoracic impedance measurements used for determining respiration rate and minute ventilation have been proposed for use in monitoring for pulmonary congestion/edema based on evaluation of respiration rate. Reference is made to commonly-assigned U.S. Pat. No. 5,957,861 issued to Combs et al., and U.S. Pat. No. 5,876,353 issued to Riff.

Intra-thoracic impedance measurements of the type typically used for minute ventilation measurements would require implementation of additional circuitry in an ICD. Generally, to determine minute ventilation using intra-thoracic impedance measurements, the impedance measurement is acquired at a sampling rate that is asynchronous with the heart rate. The use of biphasic excitation pulses has the advantage of delivering a balanced charge pulse to the drive electrode thereby preventing residual charge at the electrode-tissue interface during the relatively high sampling rate. For determining thoracic fluid content, the intra-thoracic impedance measurements need to be sampled at a rate that allows averaging or filtering of the impedance signal associated with cardiac and respiratory cycles.

Lead impedance measurements are known for use in ICDs for monitoring lead and electrode stability. Such measurements are performed using a monophasic excitation pulse that is less than the defibrillation or pacing capture threshold and is delivered during the physiological refractory period of the heart such that the excitation pulse does not capture the heart and is imperceptible to the patient. Reference is made to U.S. Pat. No. 5,755,742 issued to Schuelke et al., and U.S. Pat. No. 6,317,628 issued to Linder et al., both of which patents are incorporated herein by reference in their entirety. The monophasic excitation pulse can be synchronized with cardiac events such that the monophasic pulse occurs during sense amplifier blanking. A single impedance measurement of a particular lead pathway is generally sufficient for lead integrity evaluation.

While lead impedance monitoring methods have been incorporated in ICD systems, such methods have not previously been adapted for use in monitoring intra-thoracic impedance-related changes due to changes in thoracic fluid content. There remains a need, therefore, for a method and apparatus for measuring intra-thoracic impedance in an ICD system for the purpose of monitoring changes in a patient's fluid status. It is desirable that such a method be readily implemented in an ICD without added circuitry or complexity to the device. CHF patient's implanted with ICDs may then be advantageously monitored for changes in fluid status to allow the early detection of pulmonary congestion as well as over-dryness.

BRIEF SUMMARY OF THE INVENTION

A fluid status monitoring system for use in detecting changes in thoracic fluid content associated with congestive heart failure, which may be readily implemented in an ICD or other cardiac stimulation or monitoring device, is provided. A fluid status monitor includes impedance measuring circuitry for performing subthreshold impedance measurements at a relatively high resolution, gated with the cardiac cycle so as to remove cardiac noise and averaged or low-pass filtered over a number of cardiac cycles to remove respiratory noise.

A fluid status impedance value is determined from a series of cardiac-gated, time-averaged or low-pass filtered sub-threshold impedance measurements. In a preferred embodiment, a fluid status monitoring session is initiated manually or periodically and includes a number of impedance measurement sets acquired at predetermined intervals, each set including a predetermined number or interval of time of consecutive, cardiac-gated impedance measurements. An average impedance is calculated for each measurement set and an overall average of the impedance measurement set averages is calculated as the periodic fluid status impedance value. Diagnostic comparisons of fluid status impedance values or a determined trend of fluid status impedance values with fluid status thresholds may be made to provisionally diagnose a clinically relevant fluid content change. Such preliminary diagnosis may generate a patient warning, initiate a data transfer to an external device, or alter pacing therapies delivered by the ICD or another implantable device.

A preferred electrode configuration for making impedance measurements for use in fluid status monitoring in an ICD system includes a right ventricular coil electrode and the ICD can electrode for delivering the excitation current and measuring the resulting voltage. However, any available electrode configuration associated with the ICD system or other cardiac stimulation/monitoring device in which the present invention is implemented may conceivably be used for measuring intra-thoracic impedance for use in fluid status monitoring. The excitation and measurement pairs may be the same electrode pair or different electrode pairs.

In one embodiment, the present invention is realized in an ICD system that includes an ICD, incorporating the fluid status monitoring circuitry, and an associated set of leads. The fluid status monitoring circuitry includes fluid status monitor control circuitry, a fluid status monitor control register, an impedance measurement register, an impedance data register, and excitation pulse control circuitry. The fluid status control register and impedance measurement register receive and store parameter values from ICD control circuitry, which may be in the form of a programmable microprocessor. Parameter values stored in the control and impedance measurement registers are retrieved by fluid status monitor control circuitry for use in controlling the delivery of an excitation pulse via excitation pulse control circuitry and controlling a current monitor and voltage monitor used in measuring the delivered current and resulting voltage during an excitation pulse. ICD terminals coupled to selected excitation electrode pairs and selected measurement electrode pairs are coupled to the fluid status monitor via switching circuitry included in the ICD such that any of the available electrodes may be selected in various excitation and measurement bipolar or multipolar configurations for fluid status monitoring.

The measured current and voltage during an excitation pulse are digitized by fluid status monitor control circuitry and stored in the impedance data register for transfer to the ICD microprocessor. The microprocessor uses the acquired current and voltage data for calculating impedances from which a fluid status impedance value is then determined.

In some embodiments, a cross-check measurement pathway is used to verify a provisional thoracic fluid status change diagnosis. If a change in intra-thoracic impedance measurements performed on a primary measurement pathway is detected, such measurements or the resulting fluid status impedance value may be compared to measurement or a fluid status impedance value obtained from a cross-check measurement pathway.

DETAILED DESCRIPTION OF THE PREFERRED EMBODIMENTS

The present invention is directed toward providing thoracic fluid status monitoring for the detection of clinically relevant changes in thoracic fluid content for use in an implantable cardiac stimulation or monitoring device. It is believed that the benefits of the present invention may be fully realized in an ICD and thereby advantageously employed to monitor thoracic fluid trends in CHF patient's having an ICD. However, it is to be understood that aspects of the present invention may be usefully employed in a variety of implantable cardiac stimulation/monitoring devices. The present invention is therefore not limited to use in an ICD, though the illustrative embodiments described herein are primarily directed toward an ICD implementation.

Figure 1:
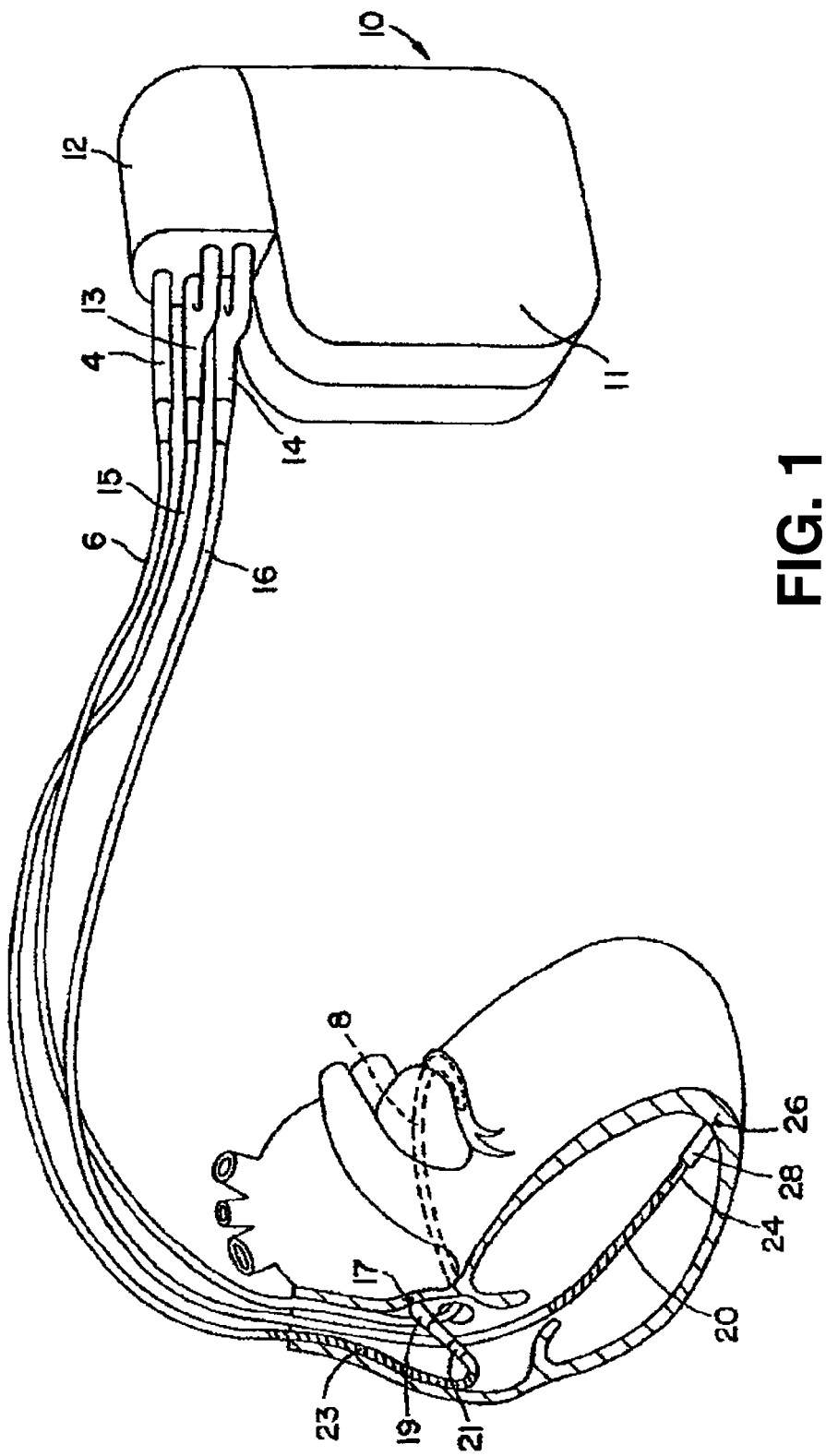
FIG. 1 is an illustration of an ICD coupled to a patient's heart by way of three leads.

FIG. 1 is an illustration of an ICD 10 coupled to a patient's heart by way of three leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 1, the right ventricular lead 16 is positioned such that its distal end is in the right ventricle (RV) for sensing right ventricular cardiac signals and delivering pacing or shocking pulses in the right ventricle. For these purposes, right ventricular lead 16 is equipped with a ring electrode 24, a tip electrode 26, which is optionally mounted retractably within an electrode head 28, and RV coil electrode 20, each of which are connected to an insulated conductor contained within the body of lead 16. The proximal end of the insulated conductors are coupled to corresponding connectors carried by a connector 14, shown here as a bifurcated connector, at the proximal end of lead 16 for providing electrical connection to ICD 10.

The right atrial lead 15 is positioned such that its distal end is in the vicinity of the right atrium (RA) and the superior vena cava (SVC). Lead 15 is equipped with a RA ring electrode 21 and a RA tip electrode 17, optionally mounted retractably within electrode head 19, for sensing and pacing in the right atrium. Lead 15 is further equipped with an SVC coil electrode 23 for delivering high-energy shock therapy. The RA ring electrode 21, RA tip electrode 17 and the SVC coil electrode 23 are each connected to an insulated conductor within the body of the right atrial lead 15. Each insulated conductor is coupled at its proximal end to a connector carried by connector 13, also shown as a bifurcated connector.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the RV coil electrode 20 or the SVC coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the defibrillation coil electrodes 8, 20 or 23 for defibrillation of the atria or ventricles.

In accordance with the present invention, any of the available electrodes 8, 17, 21, 20, 23, 24, 26, including housing 11, may be selected in pairs for use in performing impedance measurements for the purposes of monitoring thoracic fluid status. It is expected that a typical impedance measurement configuration will include one of coil electrodes 8, 20 or 23 paired with housing 11, another of coil electrodes 8, 20 and 23 or one of ring electrodes 21 or 26 as the return electrode.

It is recognized that alternate lead systems may be substituted for the three lead system illustrated in FIG. 1 having a different number or arrangement of pacing, sensing, and high-voltage electrodes in operational relation to the patient's heart. While a particular multi-chamber ICD and lead system is illustrated in FIG. 1, methodologies included in the present invention may be adapted for use with single chamber, dual chamber, or multichamber ICD systems.

Figure 2:
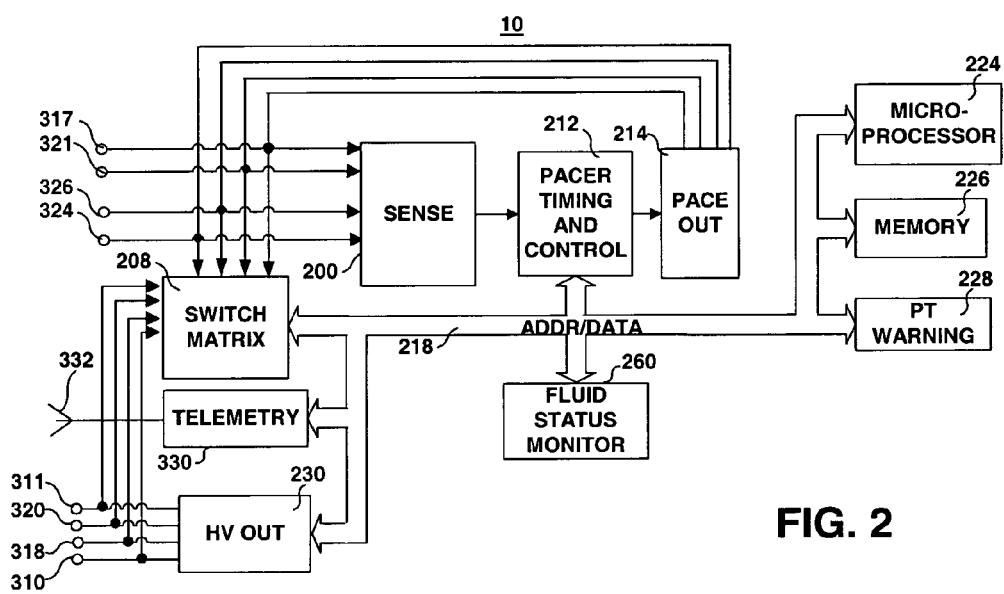
FIG. 2 is a functional block diagram of an ICD in which the present invention may usefully be practiced.

FIG. 2 is a functional block diagram of an ICD in which the present invention may be usefully be practiced. This diagram should be taken as exemplary of the type of device with which the invention may be embodied and not as limiting, as it is believed that the invention may usefully be practiced in other device implementations, such as cardioverters and defibrillators which do not provide pacing-type therapies. It is further understood that the methods included in the present invention for monitoring thoracic fluid content are not limited to implementation in defibrillation/cardioverter devices. While the methods to be described herein are readily implemented in ICD devices, such methods may be beneficially put to practice in cardiac pacing devices or devices intended for monitoring only.

The disclosed embodiment shown in FIG. 2 is a microprocessor-controlled device, but the methods of the present invention may also be practiced with devices employing custom integrated circuitry for controlling and performing device functions. For example, state machine architectures in which a state counter serves to control an arithmetic logic unit to perform calculations according to a prescribed sequence of counter controlled steps may be employed in the practice of the present invention.

It is expected that the present invention may be readily practiced using the basic hardware of existing single-, dual-, or multi-chamber ICD systems. The invention may be advantageously implemented in an ICD primarily by means of variations in the software stored in memory associated with a microprocessor-controlled ICD and adaptation of subthreshold lead impedance measurement functions, which may already be employed by the ICD system for use in monitoring lead impedances for detecting lead/electrode instability.

With regard to the electrode system illustrated in FIG. 1, the ICD 10 is provided with a number of connection terminals for achieving electrical connection to the cardiac leads 6, 15, and 16 and their respective electrodes. The connection terminal 311 provides electrical connection to the housing 11 for use as the indifferent can electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 230 to facilitate the delivery of high energy shocking pulses to the heart using one or more of the coil electrodes 8, 20, and 23 and optionally the housing 11.

The connection terminals 317 and 321 provide electrical connection to RA tip electrode 17 and RA ring electrode 21 positioned in the right atrium. The connection terminals 326 and 324 provide electrical connection to RV tip electrode 26 and RV ring electrode 24 positioned in the right ventricle. The connection terminals 317, 321, 326 and 324 are further coupled to sensing circuitry 200 for sensing cardiac signals, such as P-waves and R-waves, and classifying the heart rhythm.

Sensing circuitry 200 typically includes automatic gain controlled amplifiers with adjustable sensing thresholds, e.g., corresponding to that disclosed in U.S. Pat. No. 5,117,824, by Keimel, et al. Sensing circuitry 200 may further include signal conditioning circuitry and an analog-to-digital converter to allow digital analysis of EGM signals by microprocessor 224 to recognize and classify the patient's heart rhythm employing any of the numerous signal processing methods known in the art.

A fluid status monitor 260 includes circuitry for performing intra-thoracic impedance measurements for used in determining a fluid status impedance value as will be described in greater detail below. Excitation and impedance measurement circuitry included in fluid status monitor 260 may correspond generally to that disclosed in the above-reverenced U.S. Pat. No. 6,317,628, issued to Linder, et al., or in U.S. Pat. No. 5,755,742 to Schuelke et al. In fact, in some embodiments of the present invention, excitation and impedance measurement circuitry included in fluid status monitor 260 may perform a dual function.

At times, microprocessor 224 may initiate lead impedance measurements utilizing the excitation and impedance measurement circuitry included in fluid status monitor 260 for use in monitoring lead stability, as generally taught by the '628 and '742 patents referenced above. At other times, microprocessor 224 may initiate a fluid status monitoring session utilizing the same impedance measurement circuitry included in fluid status monitor 260. Each of the lead stability monitoring and fluid status monitoring functions utilizing the excitation and impedance measurement circuitry will follow uniquely defined monitoring algorithms defining the electrodes involved in the monitoring, the scheduling of the impedance measurements, and the processing of the measurements, as controlled by microprocessor 224 according to operating parameters stored in associated memory 226. The preferred methods used in fluid status monitoring will be fully described herein.

Fluid status monitor 260 is coupled to the various electrodes via switch matrix 208 which may be used for selecting which electrodes are employed for performing a intra-thoracic impedance measurement. Alternatively, a pair of excitation electrodes and a pair of measurement electrodes (which may be the same or different pairs) may be selected from the available electrodes by connecting the corresponding terminals 311, 320, 318, 310, 317, 321, 326, or 324 directly to fluid status monitor 260 such that the electrodes used in measuring intra-thoracic impedance are not changeable. It is preferable, however, that the excitation and measurement electrode pairs are selectable via switch matrix 208 to allow tailoring to individual patient situations and elimination of an electrode from the excitation and measurement pairs should the electrode and corresponding lead become faulty.

Intra-thoracic impedance data obtained by fluid status monitor 260 are made available to microprocessor 224 via address/data bus 218. Microprocessor 224 may further process and analyze the intra-thoracic impedance measurement data to determine a periodic fluid status impedance value and evaluate a fluid status trend. Based on a calculated fluid status impedance value or the fluid status trend, microprocessor 224 may tentatively diagnose a clinically-relevant change in fluid status and trigger a patient warning invoked in patient warning circuitry 228 to alert the patient to seek medical attention. A suitable patient perceptible, acoustic alarm that is employed in the SYNCHROMED® implantable drug administration device marketed by the assignee of the present invention may be employed as patient warning device 228. Patient warning device 228 may alternatively take the form of audible communication apparatus for use in an implantable device as generally disclosed in commonly-assigned U.S. Pat. No. 6,082,367 issued to Greeniger, et al., incorporated herein by reference in its entirety. The warning may alert the patient to a trend in the fluid status indicating the patient is developing pulmonary congestion/edema or that the patient may be over-diuresed. In either case, a physician consultation, remotely or in an office visit, regarding diuretic dosages may allow the patient's fluid status to be normalized, thereby preventing a worsening of the condition, thereby averting hospitalization.

A clinically-relevant change in fluid status tentatively diagnosed by microprocessor 224 may additionally or alternatively initiate a transmission of data from ICD 10 to an external device. Fluid status data is preferably stored in memory 226 until transmission to an external device in response to a manual interrogation of ICD 10 or a triggered data transmission. Such transmission may be initiated manually by the patient or a person attending the patient upon generation of an audible sound or other patient warning signal by patient warning device 228. Alternatively, such transmission may be initiated automatically by ICD 10 when a communication link is established with an external device upon a tentatively-diagnosed, clinically relevant, fluid status change. An external device receiving transmitted data may be, for example, an external physician programmer, a patient programmer or home monitor which may be in communication with a centralized data base, a personal computer, a centralized computer network system, or an Internet based patient data system via a modem.

The telemetry circuit 330 receives downlink telemetry from and sends uplink telemetry to an external programmer, as is conventional in implantable anti-arrhythmia devices, by means of an antenna 332. Received telemetry is provided to microprocessor 224, and data to be uplinked to the programmer and control signals for the telemetry circuit 330 are provided by microprocessor 224 via address/data bus 218. Data to be uplinked may include a record of detected arrhythmia episodes, as is customary in modern ICDs, or other detected physiologic or device-related events. In accordance with the present invention, a record of the impedance measurement data, fluid status impedance values and/or trend measured by fluid status monitor 260 may be made available via telemetry upon an interrogation command. Review of such data may be useful to a clinician in fluid status of a patient. Numerous types of telemetry systems known for use in implantable devices may be used.

The remainder of circuitry illustrated in FIG. 2 is dedicated to the provision of cardiac pacing, cardioversion and defibrillation therapies and, for the purposes of the present invention, may correspond to circuitry known in the prior art. In the exemplary embodiment shown in FIG. 2, the pacer timing and control circuitry 212 includes programmable digital counters which control the basic time intervals associated with various single, dual or multi-chamber pacing modes or anti-tachycardia pacing therapies delivered in the atria or ventricles. Pacer timing and control circuitry 212 also determines the amplitude of the cardiac pacing pulses under the control of microprocessor 224.

During pacing, escape interval counters within pacer timing and control circuitry 212 are reset upon receiving signals from sensing circuitry 200 generated upon sensing cardiac events. In accordance with the selected mode of pacing, pacing pulses are generated by pacing output circuit 214, which may be coupled to the desired electrodes for pacing via switch matrix 208. The escape interval counters are reset upon generation of pacing pulses, and thereby control the basic timing of cardiac pacing functions, which may include anti-tachycardia pacing, cardiac resynchronization therapy, extra-systolic stimulation, or other types of pacing therapies.

In response to the detection of atrial or ventricular tachycardia based on sensing operations performed by sensing circuitry 200, an anti-tachycardia pacing therapy may be delivered if desired by loading a regimen from microcontroller 224 into the pacer timing and control circuitry 212 according to the type of tachycardia detected. In the event that higher voltage cardioversion or defibrillation shock pulses are required, microprocessor 224 activates the high-voltage output circuitry 230. High-voltage output circuitry includes high voltage capacitors and a charging circuit. Timing of the delivery of a defibrillation or cardioversion high-energy pulse is controlled by pacer timing and control circuitry 212.

Turning to the fluid status monitoring operations of the present invention, fluid status monitor 260 is provided and employed in a monitor mode initiated by commands from the microprocessor 224 on address/data bus 218 either automatically on a periodic basis or in response to a programmed command received through telemetry 330. Very generally, when fluid status monitoring is initiated by microprocessor 224, an excitation or "force" terminal pair and a "measure" terminal pair are selected from among high voltage terminals 320, 318, and 310, pace/sense terminals 326 and 324 and 317 and 321, and housing 11 through connections made in switch matrix 208.

Impedance measurements are performed synchronized to cardiac sensed or paced events according to sensed event signals generated by pacer timing and control 212 and received by fluid status monitor 260 on address/data bus 218. Fluid status monitor 260 triggers an excitation pulse in response to a sensed cardiac event signal and initiates sampling of the delivered current and resulting voltage on the excitation and measurement pathways, respectively, as will be further described below. Generally, an excitation pulse will be delivered in a ventricular chamber in response to a ventricular sensed event (R-wave), as will be described in the illustrative embodiments presented herein. However, an excitation pulse may conceivably be delivered in an atrial chamber in response to an atrial sensed event (P-wave) and is not outside the scope of the present invention.

An impedance measured by fluid status monitor 260 will include the intrinsic lead resistive impedance if the excitation and measurement pathways include common electrodes. The intrinsic lead impedance may be measured between the distal electrode and the proximal connector element when the lead is not implanted. This intrinsic lead impedance is a relatively low value for a lead without any insulation defects or loose or open internal connections with the proximal connector element and the distal electrode. The impedance that is actually measured when the lead is implanted includes the tissue impedance (TI), which will vary with increasing or decreasing fluid retention and pulmonary congestion. Increased tissue fluid content will decrease the relative tissue resistance while decreased fluid content will increase the relative tissue fluid resistance contributing to an impedance measurement.

The impedance measurement may further include the electrode/tissue interface impedance (ETI), and may include any impedance caused by a loose or otherwise poor electrical connection of the proximal lead connector element with the ICD connector block. The ETI impedance may be considered a resistive impedance and varies depending on electrode surface area/shape and associated current density. The total normal impedance value ranges under normal thoracic fluid content conditions for any particular lead design and combinations of excitation and measure lead pairs may be derived empirically from clinical experience gained over time. Methods for dealing with changes in impedance measurements unrelated to changes in fluid status, i.e. changes in the ETI due to lead shifting or dislodgment or changes in the intrinsic lead impedance due to lead-related issues such as poor connection to the ICD, an insulation breach or a faulty conductor, will be addressed below.

A sub-threshold, excitation or "force" voltage pulse (Vp) of predetermined amplitude and pulse width is generated by a force pulse generator within fluid status monitor 260. The force pulse Vp is applied to one terminal included in the force terminal pair selected as the "drive" terminal while the second terminal in the force terminal pair, selected as the "return" terminal, is held at system ground. The excitation path therefore is through the driven terminal and corresponding conductor and electrode, the patient's body, in particular the thoracic region and heart tissue, the return electrode, conductor and associated terminal held at system ground. A measure path is also selected which includes a measure terminal which may be the same or different than driven terminal, the associated conductor and electrode, the thoracic region and heart tissue, and a return electrode, conductor and associated terminal at system ground. It should be noted that the force pulse Vp could be in the form of a current pulse instead of a voltage pulse, and, in either case, may consist of one or more phases of differing polarity but is preferably a monophasic, constant voltage pulse for simplicity of implementation.

The electrical current delivered to the excitation path during the delivery of the force pulse Vp is measured as a signal Im by fluid status monitor 260. At the same time, the voltage appearing across the measure terminal pair is measured as the signal Vm in fluid status monitor 260. From the measured current Im flowing into the excitation path and the measured voltage Vm induced across the measure path between the measure terminal pair, it is possible to calculate the apparent intra-thoracic impedance according to Ohm's Law. A set of measured currents Im and voltages Vm obtained during a series of cardiac cycles are employed to derive a fluid status impedance value in microprocessor 224, and infer the fluid status trend by comparison to previously measured intra-thoracic impedances and/or maximum and minimum fluid status impedance threshold values. If the force pulse is alternatively provided as a constant current pulse rather than a voltage pulse, with suitable limitations placed on the maximum current to be applied to avoid capture of the heart, the voltage and current measurements described above would be reversed, but the equivalent impedance results would be obtained.

As will be described in greater detail below, a fluid status impedance value is calculated from a series of cardiac-gated impedance measurements. The derived fluid status impedance value is then employed by microprocessor 224 in a diagnostic comparison to normal or previous impedance values in order to diagnose a fluid status trend. Generally, if the calculated fluid status impedance value is within an acceptable impedance range or the trend of consecutive, periodic fluid status impedance values is determined stable, the fluid status is presumed to be stable. However, if a fluid status impedance value or trend is greater than a maximum or less than a minimum acceptable value, the fluid status may be instable warranting clinical attention. Normal impedance values or ranges for the particular leads used for fluid status monitoring under clinically acceptable fluid status conditions can be derived in advance from characteristics of the lead type or model under test when the patient's fluid status is clinically managed to a normal state. Thresholds for defining the boundaries of clinically relevant levels of increased or decreased fluid content, based on individual patient or broader clinical experience, may be programmed and stored in memory 226 for use by microprocessor 224 during diagnostic comparisons. As will be described in greater detail below, since the excitation path and the measure path include electrode-tissue interface impedance and intrinsic lead impedance factors, a further evaluation of fluid status impedance values involving cross-reference leads may be necessary to determine if a change in the measured impedance is exhibiting lead or electrode instability rather than a fluid status change.

Whether or not a clinically-relevant fluid status change is diagnosed by microcomputer 224, the fluid status impedance data may be stored in memory 226 until an ICD interrogation is initiated. When uplinked to an external device, data may be displayed by the external device and interpreted by the physician with assistance of displayed fluid status impedance threshold values and/or an analysis program to display fluid status impedance trends. When ICD 10 includes automated lead-diagnostic functions, diagnosis of potential lead-related issues that may affect fluid status impedance trend data may also be provided for transfer and displayed.

Figure 3A:
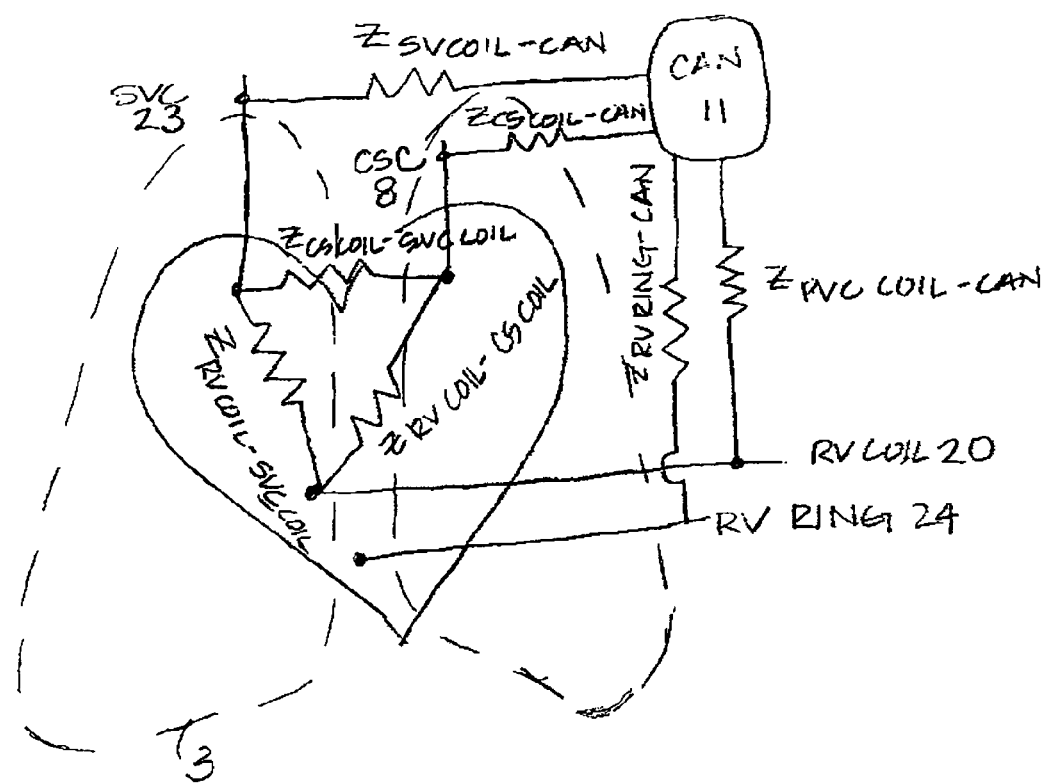
FIG. 3A is a schematic illustration of fluid status impedance measurement pathways.

FIG. 3A is a schematic illustration of fluid status impedance measurement pathways, which may be employed by fluid status monitor 260. The lungs 3 are indicated by dashed line to illustrate the approximate relative location of the lungs with respect to the intracardiac electrodes and can electrode 11. A selected intra-thoracic impedance measurement pathway should result in a measurement field that encompasses at least a portion of the thoracic volume occupied by the lungs.

Table I provides a partial listing of possible intra-thoracic impedance measurement pathways with respect to the electrode arrangement shown in FIG. 1, some of which are illustrated in FIG. 3A. The list provided in Table I and the combinations illustrated in FIG. 3A are not intended to be exclusive. Numerous electrode combinations, in either bipolar or multipolar arrangements, will be apparent to one skilled in the art and such combinations will depend on the particular lead system used. Therefore, only a partial listing of possible combinations is presented in TABLE I for the sake of illustration.

TABLE I

| EXCITATION PAIR | MEASURE PAIR |
|---|---|
| RV COIL-CAN | RV COIL-CAN |
| RV COIL-CAN | RV RING-CAN |
| RV COIL-CAN | RV TIP-CAN |
| RV COIL-SVC COIL | RV COIL-SVC COIL |
| SVC COIL-CAN | SVC COIL-CAN |
| CS COIL-CAN | CS COIL-CAN |
| SVC COIL-CS COIL | SVC COIL-CS COIL |
| RV COIL-CS COIL | RV COIL-CS COIL |

It is noted that the excitation and measurement lead pathways may often include the ICD housing 11 as the can electrode. ICD implantation sites are typically in the thoracic region and, particularly when an active can electrode is utilized, most commonly in the left pectoral region. For the purposes of the present invention, it is expected that fluid status monitoring may be successfully performed with the ICD placement, and hence can electrode placement, in either the left or right pectoral regions.

Figure 3B:
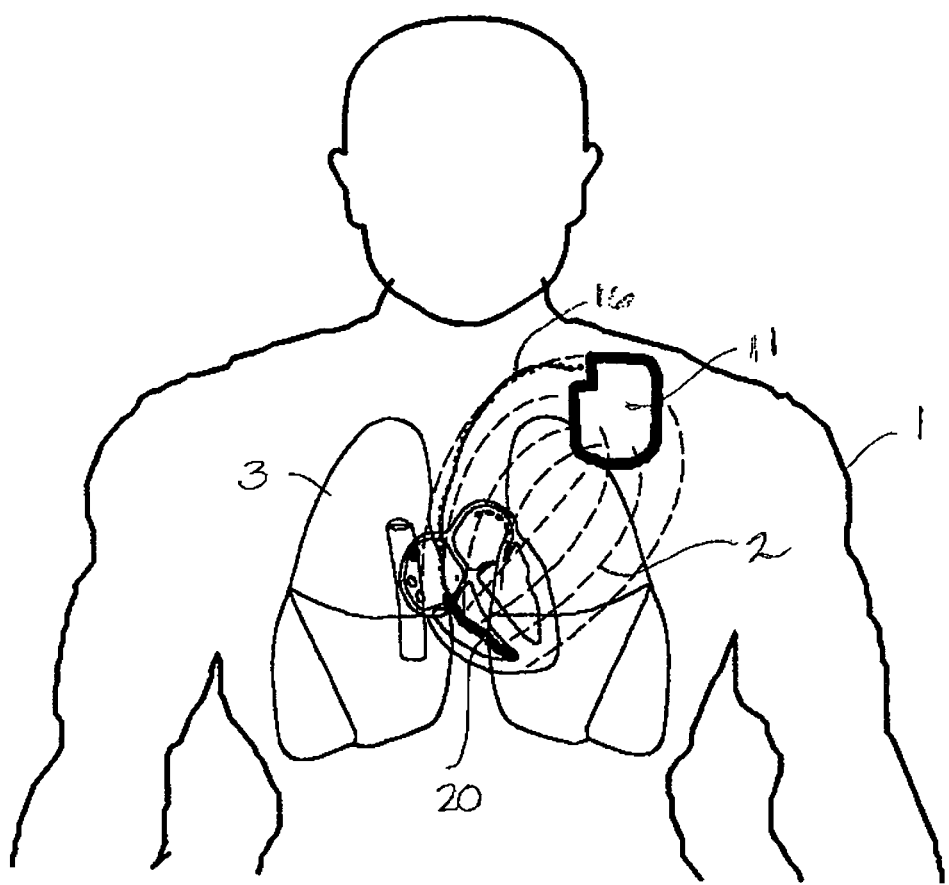
FIG. 3B is an illustration providing a conceptual view of the impedance measurement field resulting from using an RV coil-can excitation/measurement pathway.

In a preferred embodiment, intra-thoracic impedance measurements performed for the purposes of fluid status monitoring are performed using the RV coil-can configuration for both the excitation and measure pathways, resulting in a fluid status impedance value calculated based on the RV coil-can impedance measurement, $Z_{RVCOIL-CAN}$, shown in FIG. 3A. FIG. 3B is an illustration providing a conceptual view of the resulting impedance measurement field using this RV coil-can configuration. With the ICD 10 implanted in a left pectoral location of a patient 1, an intra-thoracic impedance measurement made between RV coil 20 located on RV lead 16 and the can electrode 11 will include the impedance of the heart and lung tissue present in the resulting measurement field 2 between RV coil 20 and can electrode 11.

It is recognized, as listed in Table I, however, that alternative excitation and measurement pathways may readily be employed for fluid status monitoring which will encompass a measurement field that includes the lungs 3. For example, intra-thoracic impedance measurements may alternatively be performed, as shown in FIG. 3A, by selecting SVC coil 23 with housing 11 ($Z_{SVC\ COIL-CAN}$) or CS coil 8 with housing 11 ($Z_{CS\ COIL-CAN}$) or by selection of any of the available coil electrodes 8, 20, and 23 in pairs thereby providing possible intra-thoracic impedance measurements between CS coil 8 and SVC coil 23 ($Z_{CS\ COIL-SVC\ COIL}$), between RV coil 20 and CS coil 8 ($Z_{RV\ COIL-CS\ COIL}$), or between RV coil 20 and SVC coil 23 ($Z_{RVCOIL-SVCCOIL}$). When ring electrodes are available, such as RV ring electrode 24, a ring electrode may be included in the intra-thoracic impedance measurement pathway, e.g. an RV ring 24 to housing 11 ($Z_{RV\ RING-CAN}$).

When pacing tip electrodes are available, such electrodes may also be utilized in intra-thoracic impedance measurements, e.g. the RV tip-can configuration listed in Table I. However, due to the small surface area typical of pacing tip electrodes, a relatively high contribution will be made to the intra-thoracic impedance measurement by the electrode-tissue interface impedance when the tip electrode is included in the measurement pathway, which may mask small changes in impedance due to variations in tissue fluid content. When methods of the present invention are implemented in alternative cardiac stimulation devices such as cardiac pacemakers, however, a tip electrode may be used as the drive electrode for the excitation path and the ring electrode may be used in the measurement path or vise versa.

Likewise, if a coronary sinus lead is provided with a tip and ring electrode for pacing and sensing functions in the left ventricle (LV), these electrodes may additionally be employed in performing intra-thoracic impedance measurements. For example, an LV tip-to-can excitation pathway and an LV ring-to-can measurement pathway may be selected; an LV coil-to-can excitation pathway may be selected and an LV ring-to-can measurement pathway may be selected, and so on.

Figure 4:
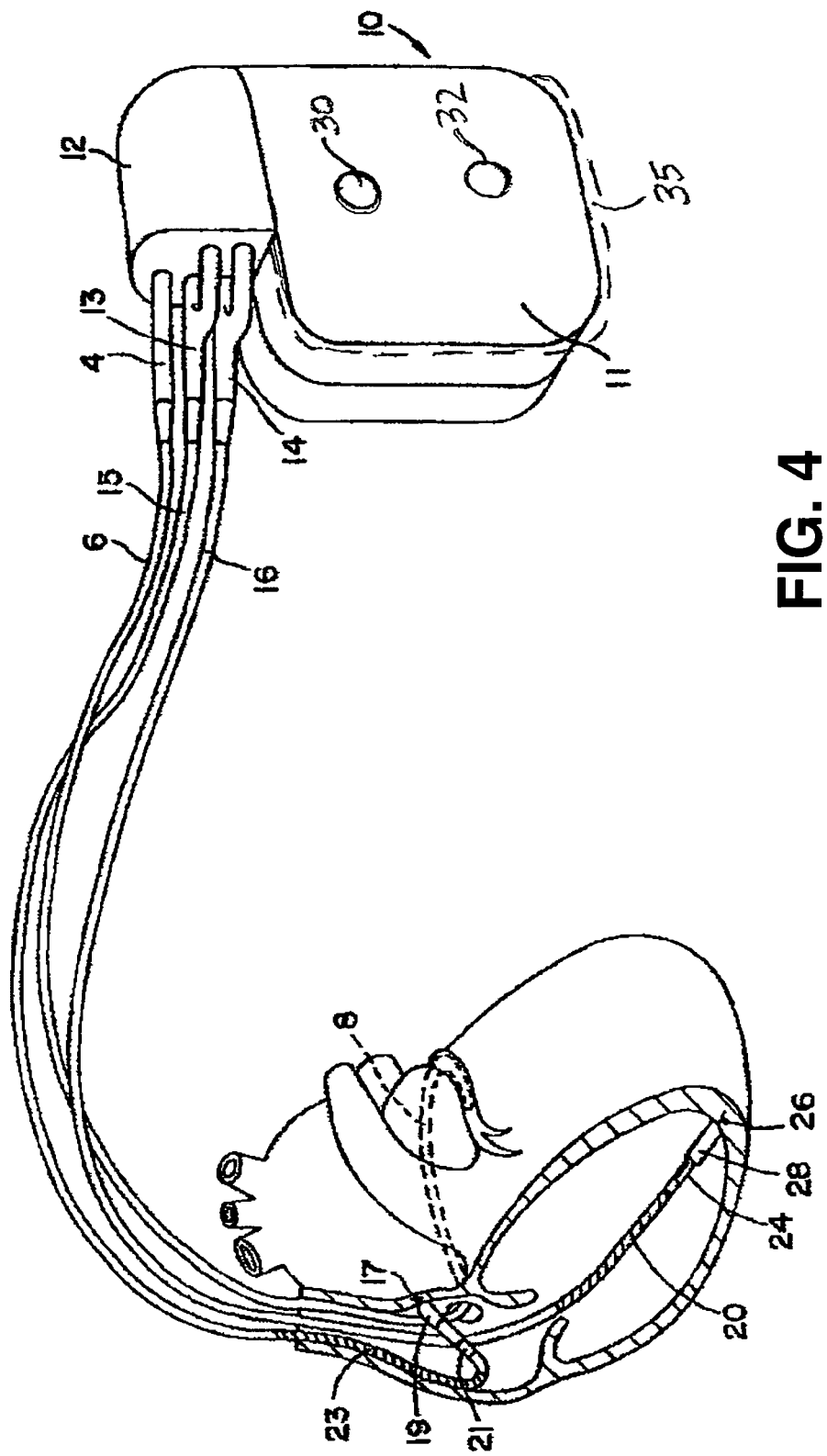
FIG. 4 is an illustration of an alternative ICD system in communication with a patient's heart by way of three leads and wherein the ICD system includes "button" electrodes incorporated on the ICD housing.

FIG. 4 is an illustration of an alternative ICD system in communication with a patient's heart by way of three leads and wherein the ICD system includes "button" electrodes incorporated on the ICD housing. In FIG. 4, ICD housing 11 is provided with an insulative coating 35, covering at least a portion of housing 11, with openings 30 and 32. The uninsulated openings 30 and 32 serve as subcutaneous electrodes which may be used for sensing subcutaneous EGG signals. An implantable system having electrodes for subcutaneous measurement of an ECG is generally disclosed in commonly assigned U.S. Pat. No. 5,987,352 issued to Klein, incorporated herein by reference in its entirety.

With regard to the embodiment shown in FIG. 4, "button" electrodes 30 and 32 may be employed in excitation and/or measurement pathways selected for measuring intra-thoracic impedance for use in monitoring thoracic fluid content. For example, an excitation pathway may be selected using the ICD terminal corresponding to RV coil electrode 20 as the "drive" terminal and one of the button electrodes 30 and 32 as the return electrode. A measure pathway may be selected using the ICD terminal corresponding to SVC coil electrode 23 or CS coil electrode 8 and the other of button electrodes 30 and 32. Such an arrangement advantageously removes the influences of parasitic resistances associated with the leads and electrodes themselves and the electrode-tissue interface from the intra-thoracic impedance measurement. It is recognized, therefore, that alternative ICD systems having subcutaneous electrodes incorporated on the ICD housing and/or positioned on subcutaneous leads extending from the ICD may advantageously employ such electrodes in intra-thoracic impedance excitation and/or measurement pathways.

Figure 5:
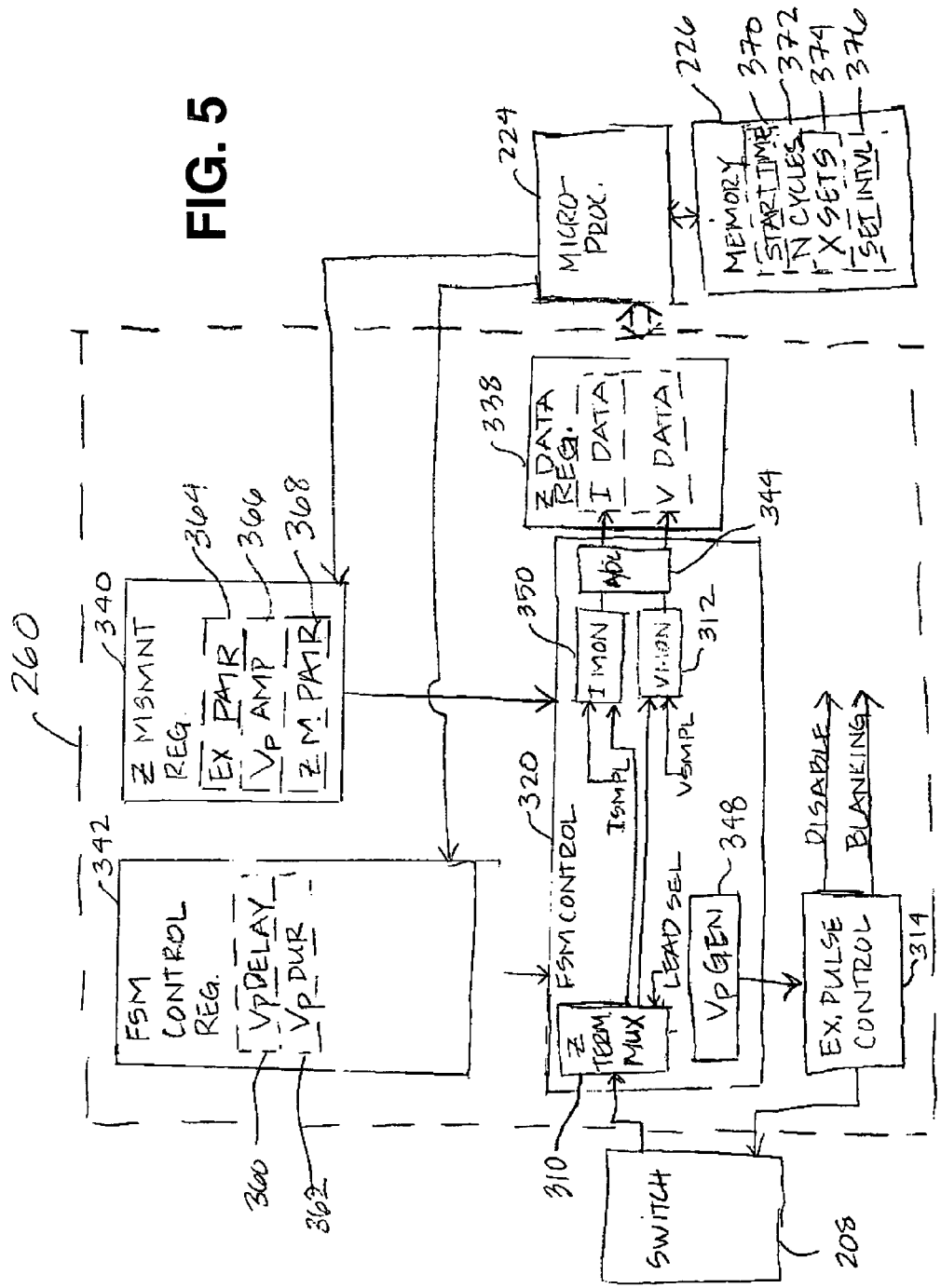
FIG. 5 is a functional block diagram of one embodiment of a fluid status monitoring circuitry.

FIG. 5 is a block diagram of one embodiment of a fluid status monitor 260. Fluid status monitor 260 includes fluid status monitor (FSM) control circuitry 320, excitation pulse control circuitry 314, a fluid status monitor control register 342, an impedance (Z) measurement register 340, and an impedance (Z) data register 338.

Fluid status monitor 260 receives input from microprocessor 224 via data bus 218 relating to fluid status monitoring control and impedance measurement parameters, which are loaded into the registers 340 and 342. Fluid status monitor control register 342 stores an excitation pulse (Vp) delay 360 for setting the delay following a ventricular sensed or paced event after which an excitation pulse will be delivered to an excitation terminal. Selected excitation terminal pair bits 364 are stored in impedance measurement register 340. Fluid status monitor control register 342 further stores an impedance measurement pulse (Vp) duration 362 defining the width of the excitation pulse to be delivered.

In addition, and in accordance with the present invention, a fluid status monitoring session start time 370 and the number of cardiac cycles, N, 372 during which cardiac-gated intra-thoracic impedance measurements will be made encompassing a "measurement set", will be stored in memory 226 associated with microprocessor 224. Rather than storing a specified number of cardiac cycles, N, during which cardiac-gated impedance measurements are performed, an interval of time during which cardiac-gated measurements are performed may be stored. A number of measurement sets, X, 374 to be included in a fluid status monitoring session and the time interval 376 between the onset of measurement sets are also stored in memory 226.

Impedance measurement register 340 stores the excitation terminal selection 364, as noted above, and the excitation pulse (Vp) amplitude 366, and impedance measurement terminal selection 368. When a fluid status monitoring session is initiated by microprocessor 224 according to stored start time 370 (or a manually initiated session), FSM control 320 retrieves the Vp delay and duration bits 360 and 362 from FSM control register 342 to deliver an excitation pulse, generated by excitation pulse generator 348, at the appropriate time via excitation pulse control circuitry 314. The selected excitation terminal pair is selected via switch 208 by impedance (Z) terminal multiplexor 310 according to the excitation terminal selection bits 364 stored in impedance measurement register 340

Excitation pulse control circuitry 314 additionally provides atrial blanking signals to be applied to ICD sensing circuitry 200 during the applied excitation pulse, as will be further described below. A disable signal may also be generated by excitation pulse control 314 to cause microprocessor 224 to disable cardioversion/defibrillation shock delivery during the impedance measurement.

Lead impedance multiplexor 310 receives input from switch 208 and the signals from selected terminals are coupled to current monitor (I MON) 350 and voltage monitor (V MON) 312. Current monitor 350 and voltage monitor 312 are enabled at the appropriate time by current sampling (ISMPL) and voltage sampling (VSMPL) signals generated within FSM control 320.

The voltage induced across the selected measurement terminal pair is measured and digitized by analog-to-digital converter 344. Digitized voltage measurements are stored in a voltage data register (V DATA) included in impedance data register 338. Likewise, the current delivered to the drive terminal is measured by current monitor 350 and digitized and stored in a current data register (I DATA) included in impedance data register 338.

An interrupt from FSM control 320 signals microprocessor 224 that the impedance measurement data (I DATA and V DATA) are stored for the given cardiac cycle. Data stored in impedance data register 338 may then be transferred to microprocessor 224 for use in calculating a measured impedance according to Ohm's Law. Measured impedances stored in memory 228 during a fluid monitoring session are then used for deriving a fluid status impedance value as will be described in greater detail below.

During a measurement set, an impedance measurement will commence on the next cardiac cycle, after an intervening paced or sensed event and the attendant delay. The impedance measurement process repeats, as will be described in greater detail below, for each cardiac cycle until the number of measurement cycles, N, 372 has been executed thereby completing one impedance measurement set. The next impedance measurement set commences after the prescribed set interval 376 has expired. When the required number of impedance measurement sets has been completed, the fluid status monitoring session is exited, and microprocessor 224 may proceed with calculating and storing a fluid status impedance value.

Microprocessor 224 will initiate subsequent fluid status monitoring sessions periodically or upon a programmed command. The resultant fluid status impedance values will be stored in memory 226, and if the stored values indicate a worsening condition based on diagnostic comparisons performed by microprocessor 224, microprocessor 224 may trigger a patient warning, initiate a data transfer, or alter a pacing therapy delivered by ICD 10 or by another implanted device such as a drug pump, in telemetric communication with ICD 10.

In one preferred embodiment, daily fluid status monitoring sessions are performed and the resultant fluid status impedance value is stored in a rolling buffer in memory 226, preferably capable of storing up to one year or more of daily fluid status measurements. The data may optionally be compressed into weekly (or other extended interval) high and low and/or mean or median measurements thereafter and accumulated for a relatively long period, e.g. years, in memory 226.

Figure 6:
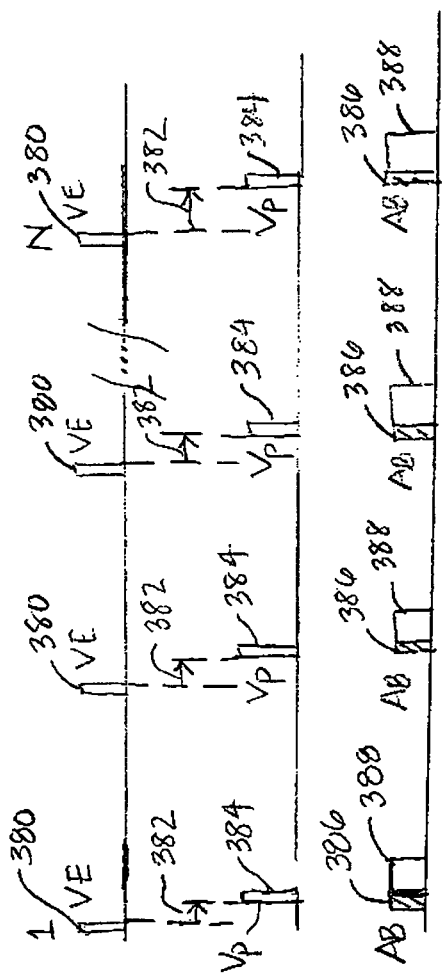
FIG. 6 is a timing diagram illustrating the delivery of a fluid status monitoring excitation pulse relative to cardiac events.

FIG. 6 is a timing diagram illustrating the timing of a fluid status monitoring excitation pulse relative to cardiac events. A series of ventricular events (VE) 380, which may be paced or sensed ventricular events, are shown along the top time line. An excitation pulse (Vp) 384 is delivered after a specified delay 382 following each ventricular event 380 during a measurement set. In a multi-chamber ICD system capable of biventricular pacing, an inter-ventricular pacing interval, often referred to as a "V-V interval" that is equal to the excitation pulse delay is either eliminated from the available V-V interval programmable values or automatically adjusted to a different interval during a fluid status monitoring session so as to prevent the simultaneous attempt by the ICD to deliver both a ventricular pacing pulse and an excitation pulse. Alternatively, excitation pulse delivery may be restricted to delivery after the later of the two ventricular pacing pulses is delivered during biventricular pacing. The excitation pulse duration and pulse amplitude are selected such that the resulting pulse energy is below the defibrillation and pacing capture threshold.

As an added safeguard against capturing the heart, the excitation pulse is preferably delivered within the physiological refractory period following the triggering cardiac event. Furthermore, the intra-thoracic impedance measurement is preferably measured at a point in time when the heart volume is not rapidly changing. The blood volume of the heart will contribute to the impedance measurement, and therefore if an impedance measurement is taken during the rapid ejection phase of systole, the rapidly changing heart blood volume may add undesirable variation to the impedance measurement. An intra-thoracic impedance measurement for purposes of monitoring for pulmonary congestion/edema or dryness, therefore, is preferably performed when the rate of change in cardiac volume (dV/dt) is near a minimum, such as: during the early, isovolumic phase of cardiac systole, late systole near the end of ejection, prior to rapid filling during diastole, or at the end of diastole, prior to the start of systole.

Since an excitation pulse delivered very late in systole or very early in diastole may inadvertently fall within the so-called "vulnerable period," a period in which stimulation may induce an arrhythmia in arrhythmia prone patients, the safest approach is to deliver the excitation pulse during the early isovolumic phase of systole, or at the end of diastole. In a preferred embodiment, the excitation pulse is delivered about 28 ms after a ventricular event. A monophasic excitation pulse is preferably delivered during the ventricular blanking interval that normally follows a ventricular paced or sensed event so as to prevent saturation of the ventricular sense amplifiers included in ICD sensing circuitry 200 (shown in FIG. 2) by the excitation pulse. Therefore, delivering the excitation pulse a very short interval, e.g. 10 to 30 ms, after a cardiac event advantageously ensures that the pulse doesn't capture the heart since it is delivered within physiologic refractory; minimizes variation due to changing blood volume of the heart since it is delivered before the rapid ejection phase, and eliminates the need for additional ventricular sense amplifier blanking.

It is contemplated that an excitation pulse could alternatively be delivered just prior to a scheduled pacing pulse, such that the impedance measurement is made at the end of diastole. Necessary sense amplifier blanking could be initiated with the delivery of the excitation pulse and continue as needed during and after the scheduled pacing pulse. Since the myocardial tissue will not be in physiologic refractory at the end of diastole, however, an excitation pulse delivered prior to a scheduled pacing pulse should be of insufficient energy to capture the heart.

Blanking of atrial sense amplifiers included in sensing circuitry 200, however, may be required during excitation pulse 384 delivery. In one embodiment, an absolute blanking interval 386 of 1.25 ms is applied to atrial sensing circuitry during excitation pulse 384 delivery followed by an optional reduced atrial sensitivity interval 388. For example a reduced atrial sensitivity interval of about 30 ms may be set depending on the programmed atrial sensitivity. If the programmed atrial sensitivity is high, a reduced atrial sensitivity interval 388 may follow the absolute atrial blanking interval 386. If the programmed atrial sensitivity is low, a reduced atrial sensitivity interval may not be necessary and only an absolute atrial blanking interval 386 is applied to prevent saturation of the atrial sense amplifiers included in sensing circuitry 200 during excitation pulse 384 delivery.

As shown in FIG. 6, excitation pulses 384 are delivered following a predetermined number, N, of consecutive ventricular events 380. The impedance measured for each of these N cycles, will be stored as one set of impedance measurements. An average impedance will be calculated for each set of impedance measurements collected, and this average will be used in calculating a fluid status impedance value. The cardiac-gated impedance measurements, i.e., impedance measurements acquired at a fixed time point relative to the cardiac cycle, will not vary due to the heart volume or motion. By averaging a series of cardiac-gated impedance measurements obtained sequentially over more than one respiration cycle, respiratory influences on the impedance measurement are removed. The fluid status impedance value derived from these time-averaged, cardiac-gated impedance measurements will therefore reflect the tissue impedance, which will vary with varying fluid content, assuming electrode and lead stability.

Thus, the cardiac-gated, intra-thoracic impedance measurements included in the fluid status monitoring methods provided by the present invention have at least two advantages over alternative intra-thoracic impedance measurement methods. First, the cardiac-gated measurements allow monophasic impedance measurements to be performed during sense amplifier blanking and may therefore be readily implemented in ICD systems already employing monophasic impedance measurement circuitry for use in lead diagnostic functions. Second, the cardiac-gated measurements reduce the number of impedance measurements that need to be performed if conventional averaging or filtering of impedance signals is applied to eliminate cardiac noise. In the methods provided herein, one intra-thoracic impedance measurement may be performed per cardiac cycle with a measurement set preferably extending over at least one respiration cycle to thereby eliminate respiration noise when a number of sets are averaged. If cardiac-gated measurements are not performed, a high-rate of impedance measurements would be required for sampling impedances at multiple time points within a cardiac cycle in order to filter cardiac noise. While such high-rate sampling may be possible, the use of biphasic or multiphasic excitation pulses may then be required to prevent imbalanced charge accumulation and, as such, more complex impedance measurement circuitry will be required.

Monophasic pulses, or non-charge balanced pulses, can lead to electrode corrosion over time. However, by reducing the required sampling rate of impedance measurements by way of the cardiac-gating techniques described herein, electrode corrosion is not expected to occur within the expected useful life of the implanted system. Furthermore, sampling rate reduction by way of cardiac-gating advantageously reduces the current demand placed on the device power supply, thereby preserving battery longevity.

Figure 7:
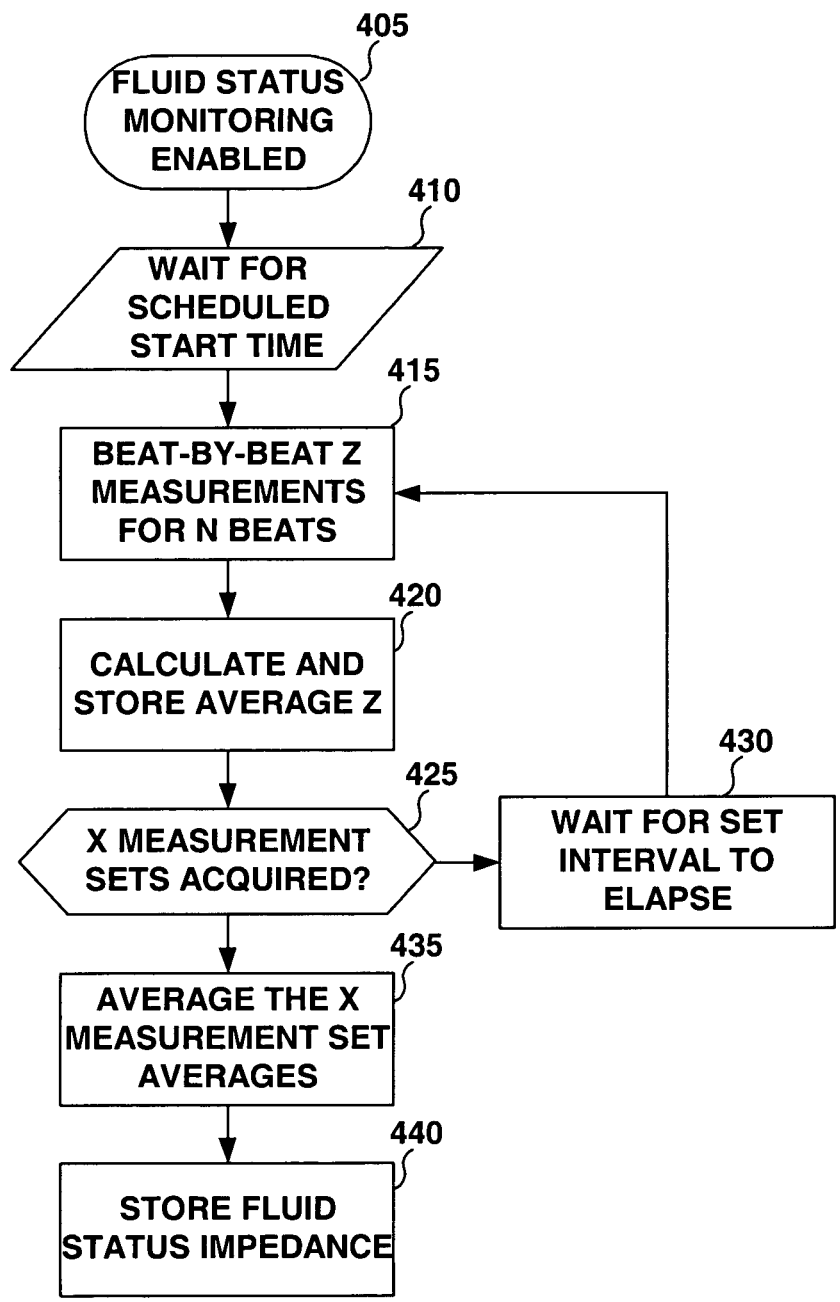
FIG. 7 is a flow chart summarizing the algorithmic steps performed during a fluid status monitoring session.

FIG. 7 is a flow chart summarizing the algorithmic steps performed during a fluid status monitoring session. Fluid status monitoring sessions will only be initiated by microprocessor 224 if fluid status monitoring is programmed to be enabled for periodic monitoring or if a programmed command is entered by a user to initiate a fluid monitoring session. When automated fluid status monitoring is enabled, as indicated by block 405, microprocessor 224 will initiate a fluid status monitoring session according to a scheduled time as indicated by step 410.

A starting time may be at a particular time of day, e.g., 12:00 pm, based on a real-time clock or based on a 24-hour timer included in ICD 10. Diurnal variation in fluid retention is typical in CHF patients, therefore fluid status monitoring sessions may be initiated at multiple and/or varying times of day to capture diurnal variations.

Upon initiating a session, a set of cardiac-gated impedance measurements are acquired at step 415 in the manner described above for a programmable number of cardiac cycles, N. For example, impedance measurements may be made during 4, 8, 16, 32, 64 or 128 consecutive cardiac events. After completing a measurement set, the stored impedance data including measured currents and measured voltages are used by microprocessor 224 at step 420 to calculate the N impedance values according to Ohm's Law and determine a measurement set average impedance. The measurement set average impedance is then stored in memory 226.

At decision step 425, a determination is made whether all scheduled measurement sets have been acquired. If not, the set interval defining the time between the onset of measurement sets is allowed to elapse at step 430, after which the next set of impedance measurements will be initiated by returning to step 415. In an exemplary embodiment, 16 measurement sets including 32 cardiac-gated measurements each are obtained at 20 minute intervals on a daily basis. It is recognized that numerous variations of scheduled fluid status monitoring session schemes may be conceived by varying the session start time, session periodicity, the number of measurements within a set, the number of sets, and/or the set interval.

After executing all (X) scheduled measurement sets and calculating an average impedance for each, an overall average of the X measurement set average impedances is calculated at step 435. This overall average is stored at step 440 as the daily, or other monitoring interval, fluid status impedance value with a corresponding time and date stamp and any other desired device-related or physiologic data. In a preferred embodiment, impedance measurement data are stored and fluid status impedance calculations are made such that the fluid status impedance may be determined with a resolution of 0.5 ohms or finer.

Figure 8:
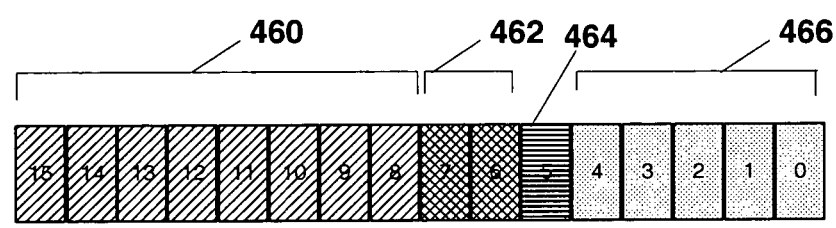
FIG. 8 is an illustration of a 16-bit storage format used for storing daily fluid status impedance values.

In one embodiment, daily fluid status impedance values are stored in a 16-bit format as shown in FIG. 8. The integer portion of the daily fluid status impedance is stored in bits 15-8 (460). The fractional portion of the daily fluid status impedance is stored in bits 7-6 (462) with bit 7 indicating 0.5 ohms when set and bit 6 indicating 0.25 ohms when set. Bit 5 (464) is set when a measurement set is discarded due to an out-of-range measurement as will be described in greater detail below. The number of valid measurement sets used in calculating the fluid status impedance is stored in bits 4-0 (466).

Figure 9A:
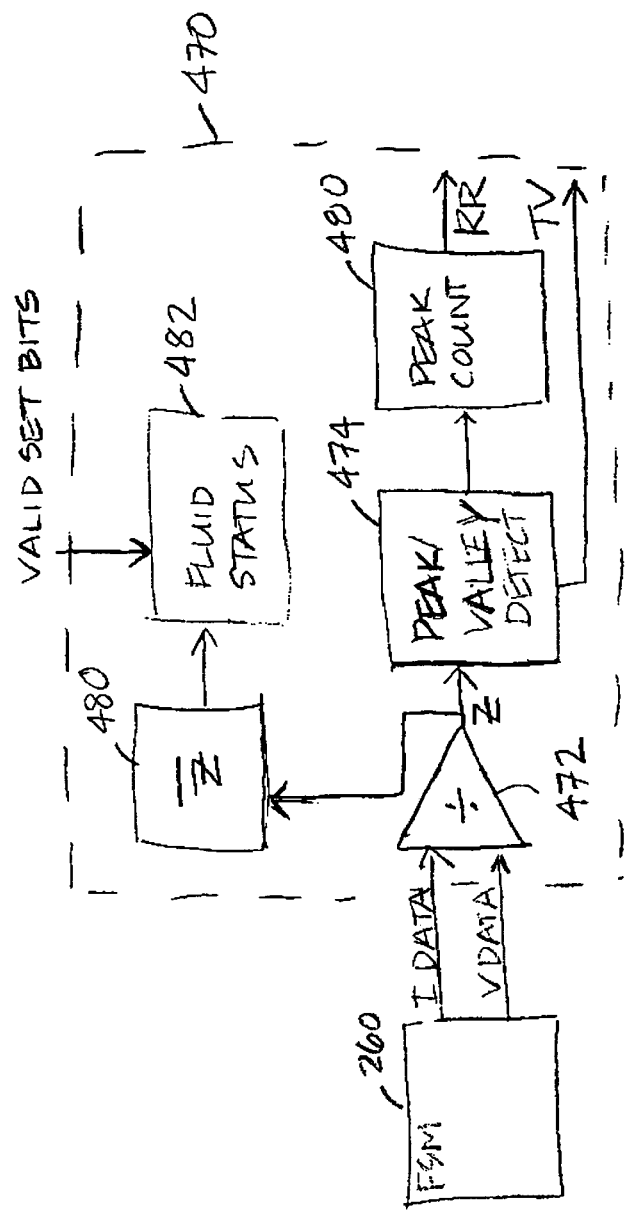
FIG. 9A is a functional block diagram illustrating the derivation of a fluid status parameter and a respiration rate from cardiac-gated impedance measurements.

FIG. 9A is a functional block diagram illustrating the derivation of a fluid status parameter and a respiration rate from cardiac-gated impedance measurements. Changes in respiration rate may also be of diagnostic or prognostic value to a physician. Increased pulmonary congestion may cause an increase in respiration rate. Patients suffering from CHF may experience episodes of Cheyne-Stokes breathing or sleep apnea. Such cardiac-related breathing disorders may indicate a worsening clinical condition. Changes in lung volume during a respiration cycle will be reflected by the beat-to-beat variation in cardiac-gated impedance measurements.

In FIG. 9A, fluid status monitor 260 provides the digitized current data (I DATA) and voltage data (V DATA) acquired during a measurement set to microprocessor 224 for use in performing the operations shown within the dashed box 470. Impedance is calculated from the current and voltage data received following each cardiac-gated measurement at block 472. This impedance is provided to a peak/valley detector 474 such that the number of peaks occurring during the measurement set may be counted by counter 480 as the respiration rate (RR). The tidal volume (TV) could also be estimated based on the amplitude change between detected peaks and valleys.

The impedance calculated at block 472 is additionally provided to block 480 which determines the average of all impedances measured during an impedance set. The measurement set averages are provided to block 482 for calculating a fluid status value as described previously. Block 482 may additionally retrieve the valid set bits indicating the number of valid measurement sets executed such that the fluid status parameter may be calculated as the overall average of the measurement set averages as described above.

Figure 9B:
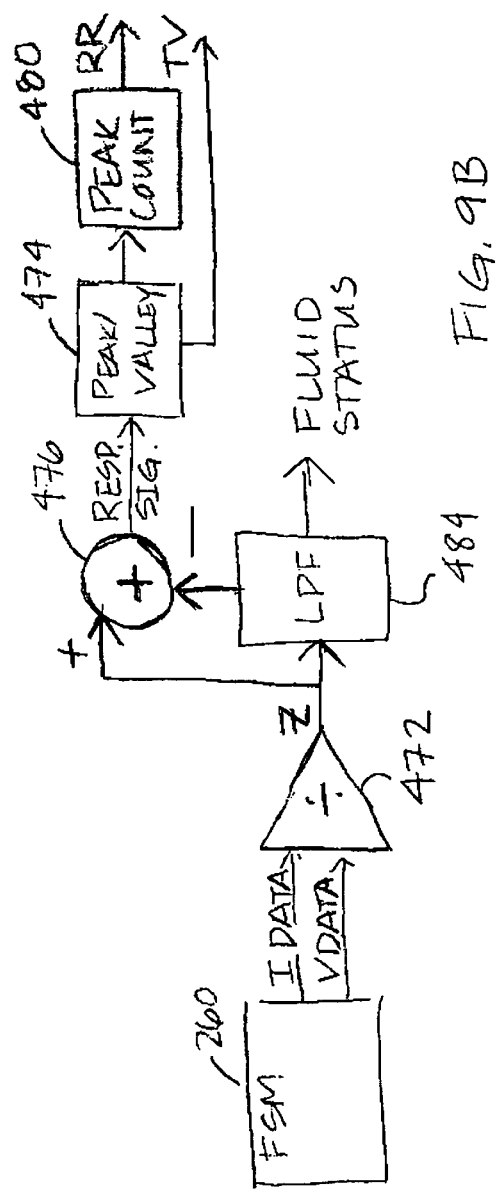
FIG. 9B is a functional block diagram depicting an alternative method for deriving a fluid status parameter and a respiration rate from cardiac-gated impedance measurements.

FIG. 9B is a functional block diagram depicting an alternative method for deriving a fluid status parameter and a respiration rate from cardiac-gated impedance measurements. In FIG. 9B, current and voltage data are provided to block 472 for determination of the measured impedance. The measured impedances are low-pass filtered at block 484 with the output provided as a fluid status signal free of cardiac, respiratory and extraneous high-frequency noise. The output of the measured impedance block 472 may additionally be provided as the positive input to a summation block 476. The output of low pass filter 484 is provided as negative input to summation block 476. The output of summation block 476 is the difference between the raw Z signal and the low-pass filtered Z signal, which will be primarily related to the influence of respiration alone. This respiration signal may be provided as input to a peak/valley detector 474 for deriving a respiration rate (RR) or be used for deriving a tidal volume (TV).

Thus, respiration rate and/or a fluid status impedance value may be determined from a series of cardiac-gated impedance measurements. Respiration rate and fluid status impedance values may both be stored in memory 226 for later review by a clinician for diagnostic, prognostic, and therapy optimization purposes.

Figure 10:
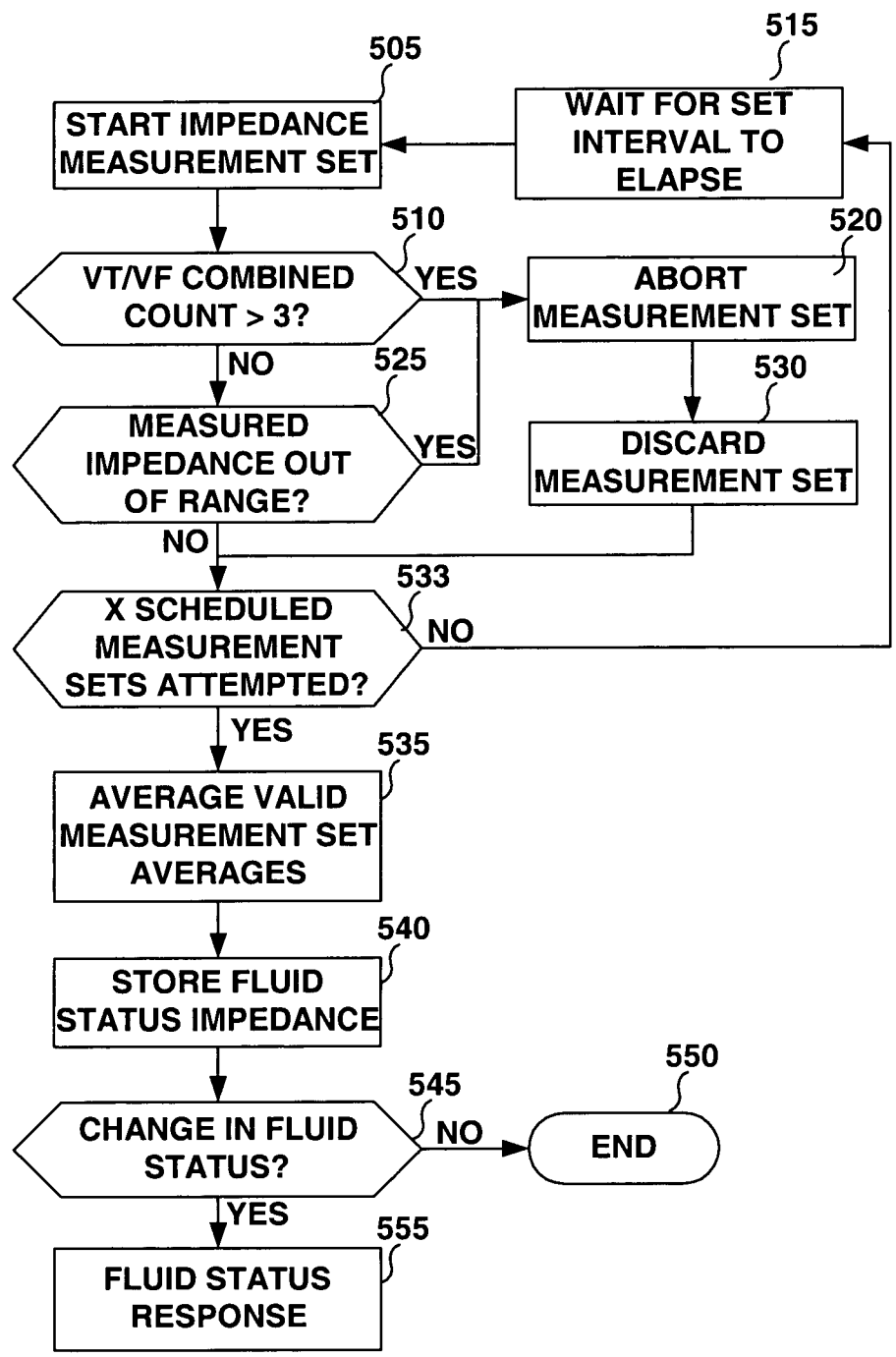
FIG. 10 is a flow chart providing an overview of operations performed during a fluid status monitoring session to ensure valid fluid status measurement values and further ensure that fluid status monitoring does not interfere with critical, life-saving therapies provided by the ICD.

FIG. 10 is a flow chart providing an overview of operations performed during a fluid status monitoring session to ensure valid fluid status measurement values and further ensure that fluid status monitoring does not interfere with critical, lifesaving therapies provided by the ICD. A fluid status monitoring session is not initiated if an anti-arrhythmia therapy is in progress (or during arrhythmia detection just prior to a therapy delivery or sustained detection after an arrhythmia therapy). Cardioversion and defibrillation shock delivery is normally disabled during intra-thoracic impedance measurements. However, monitoring for arrhythmias is preferably not suspended during a fluid monitoring session.

As such, after an impedance measurement set has been initiated at step 505, if microprocessor 224 determines at any time during the measurement set that an arrhythmia may be occurring before detection and rhythm classification is made, the measurement set is aborted at step 520. For example, if a ventricular tachycardia (VT) or ventricular fibrillation (VF) interval count is greater than a predetermined number, which may be a number less than the required number of VT or VF intervals for arrhythmia detection, the measurement set will be aborted. In a preferred embodiment, if a combined VT and VF interval count is greater than 3, as indicated by decision step 510, the measurement set is aborted at step 520. Any impedance values stored during partial execution of the measurement set will be discarded at step 530.

If all scheduled measurement sets have not yet been attempted, as determined at decision step 533, method 500 will proceed to step 515 to wait for the current set interval to elapse. There after, if no ongoing arrhythmia detection or anti-arrhythmia therapy is in progress, the next subsequent impedance measurement set will be initiated.

As long as precluding arrhythmia detection-related criteria are not satisfied at step 510 during a measurement set, the measurement set continues to be executed. If any measured impedance obtained during a measurement set is outside an acceptable impedance range, as determined at decision step 525, the measurement is considered invalid. The measurement set is aborted at step 520 and any stored data for the aborted measurement set is discarded at step 530. For example, in a preferred embodiment employing the RV coil to can excitation/measurement terminal pair, if a measured impedance is outside the range of about 20 to about 200 ohms, the measurement set is aborted at step 520. An impedance outside an acceptable range for the particular type of lead(s) used in the intra-thoracic impedance measurement may indicate lead or electrode instability. Such lead or electrode instability may render the impedance measurement invalid for use in calculating a fluid status impedance value.

In a preferred embodiment, a discarded measurement set is not re-attempted. The fluid monitoring session proceeds to the next scheduled measurement set and the final calculation of the fluid status impedance value will be based on the valid measurement sets collected which may be a number less than the number of scheduled measurement sets, X. Alternatively, a minimum number of measurement sets may be required to calculate a fluid status impedance. As such, when a measurement set is discarded, a predetermined number of repeated attempts may be performed to obtain a valid measurement set prior to the next scheduled measurement set. Alternatively, an extra measurement set may be appended to the last scheduled measurement set.

Once all scheduled measurement sets have been attempted, as determined at decision step 533, the overall average of the valid measurement set averages is calculated at step 535 and stored as the fluid status impedance at step 540 in the manner described previously.

If the fluid status impedance has changed, a preliminary diagnosis of a change in tissue fluid content may be made based on diagnostic comparisons performed by microprocessor 224 at step 545. If no tentative diagnosis of a clinically relevant change in fluid status is made at decision step 545, the fluid status monitoring session is terminated at step 550. If a change is evaluated to be clinically relevant, microprocessor 224 may initiate a fluid status response at step 555. Such responses, as noted earlier, may include one or more, but is not limited to the following: a patient alert, a data transmission, a change in pacing therapy, or a change in other types of therapy delivered by an implantable device such as a medical therapy delivered by a drug pump.

The preferred embodiments of the present invention allow fluid status monitoring to be conducted within an ICD system without the need for additional complex circuitry. Existing circuitry included in an ICD system known for use in performing subthreshold lead impedance tests may be readily adapted for use in performing fluid status monitoring by setting control parameters and a control program for scheduling a series of cardiac-gated impedance measurement sets. The use of a scheduled series of cardiac-gated impedance measurements for determining a time-averaged impedance from which a fluid status may be derived, however, is not limited to the type of subthreshold lead impedance measurement circuitry described herein. Other types of impedance measurement circuitry, including impedance measurement circuitry which utilizes biphasic or multiphasic excitation voltage or current pulses may also be utilized in conjunction with the present invention.

While the present invention has been described in the context of an ICD system, aspects of the present invention may be beneficial in other types of implantable devices, including other types of cardiac stimulation devices. Aspects of the present invention may be usefully employed in implantable devices used for monitoring a patient condition wherein tissue fluid content is of particular diagnostic or prognostic interest. Aspects of the present invention may be usefully employed in implantable devices used for treating a patient condition characterized by symptoms of fluid retention or fluid loss such that therapies may be adjusted, either automatically or by a clinician, in order to stabilize a patient's fluid status.

Although the system and method described above provides the fluid status impedance and fluid status trend determination from the measured current and voltage values to be determined within the implantable system for storage in device memory and/or transmission to an external programmer, it will be understood that the measured current and voltage values could instead be stored and transmitted out for conversion to fluid status impedance values in an external device.

As noted previously, a measured impedance will include tissue impedance, which will vary with fluid content, and the inherent lead impedance and electrode-tissue interface impedance, both of which can change due to lead-related issues such as dislodgement, insulation breach, conductor fracture, etc. Therefore, in some embodiments of the present invention, a lead impedance cross-reference check may be performed prior to making a tentative diagnosis of a clinically relevant fluid status trend in order to verify that a change in the fluid status impedance value is not due to a lead-related impedance change.

Figure 11:
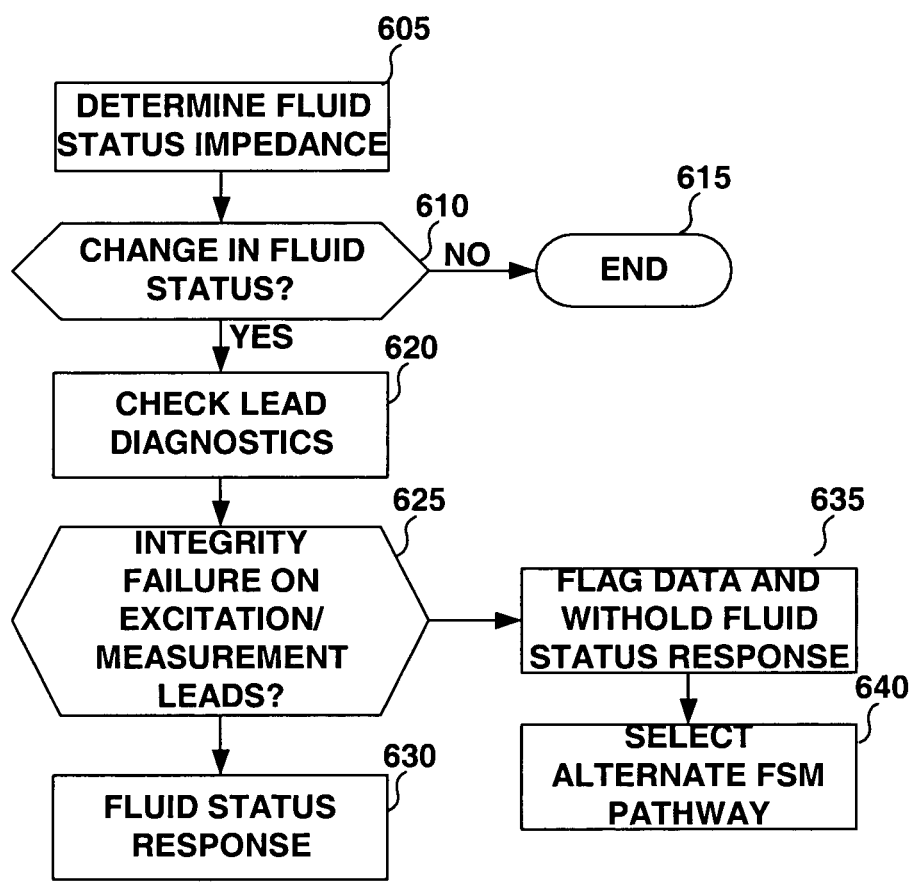
FIG. 11 is a flow chart providing an overview of a fluid status monitoring method that includes a lead impedance cross-check.

FIG. 11 is a flow chart providing an overview of a fluid status monitoring method that includes a lead impedance cross-check. At step 605, a fluid status impedance value is determined. The fluid status impedance value is preferably obtained using the methods described herein for time-averaged, cardiac-gated impedance measurements. However, the method shown in FIG. 11 is not limited to implementation with time-averaged, cardiac-gated measurements but may also be utilized in conjunction with any methods known in the art for use in deriving a monitoring parameter related to tissue fluid content or fluid congestion from impedance measurements. If a clinically-relevant change in fluid status is diagnosed at decision step 610 based on the fluid status value determined at step 605, an examination of lead integrity is performed at step 620.

Lead integrity tests based on impedance measurements are known for use in cardiac pacemakers and ICDs. Stored results of lead integrity tests may be examined at step 620 to determine if any lead integrity issues have been diagnosed. Alternatively, a lead integrity test may be triggered by the tentatively diagnosed change in fluid status to verify that at least the leads used in performing impedance tests for fluid monitoring are not suspect of lead integrity failure.

If a lead integrity issue is not diagnosed for the excitation/measurement pathways used for fluid status monitoring, as determined at decision step 625, a fluid status response 630 may be generated. The tentatively diagnosed fluid status change is deemed valid based on a lack of evidence of lead-related impedance changes.

If a lead integrity failure is diagnosed at step 625, based on a previous or triggered lead integrity test, the fluid status impedance data is flagged as questionable data at step 635, and the fluid status response is withheld. The diagnosis of a lead integrity failure may elicit an appropriate response to the lead test diagnosis in accordance with the lead integrity monitoring system employed.

At step 640, an alternate excitation and impedance measurement pathway is selected for use in subsequent fluid status monitoring (FSM) sessions. The alternate pathway should not include a suspect lead in the pathway. A "suspect lead" refers to, in this situation, an electrode, its associated conductor, connector and the connection to a terminal in the implanted device wherein the integrity of the electrical continuity between or the insulation of these components is suspected to have failed based on a lead integrity test.

Figure 12:
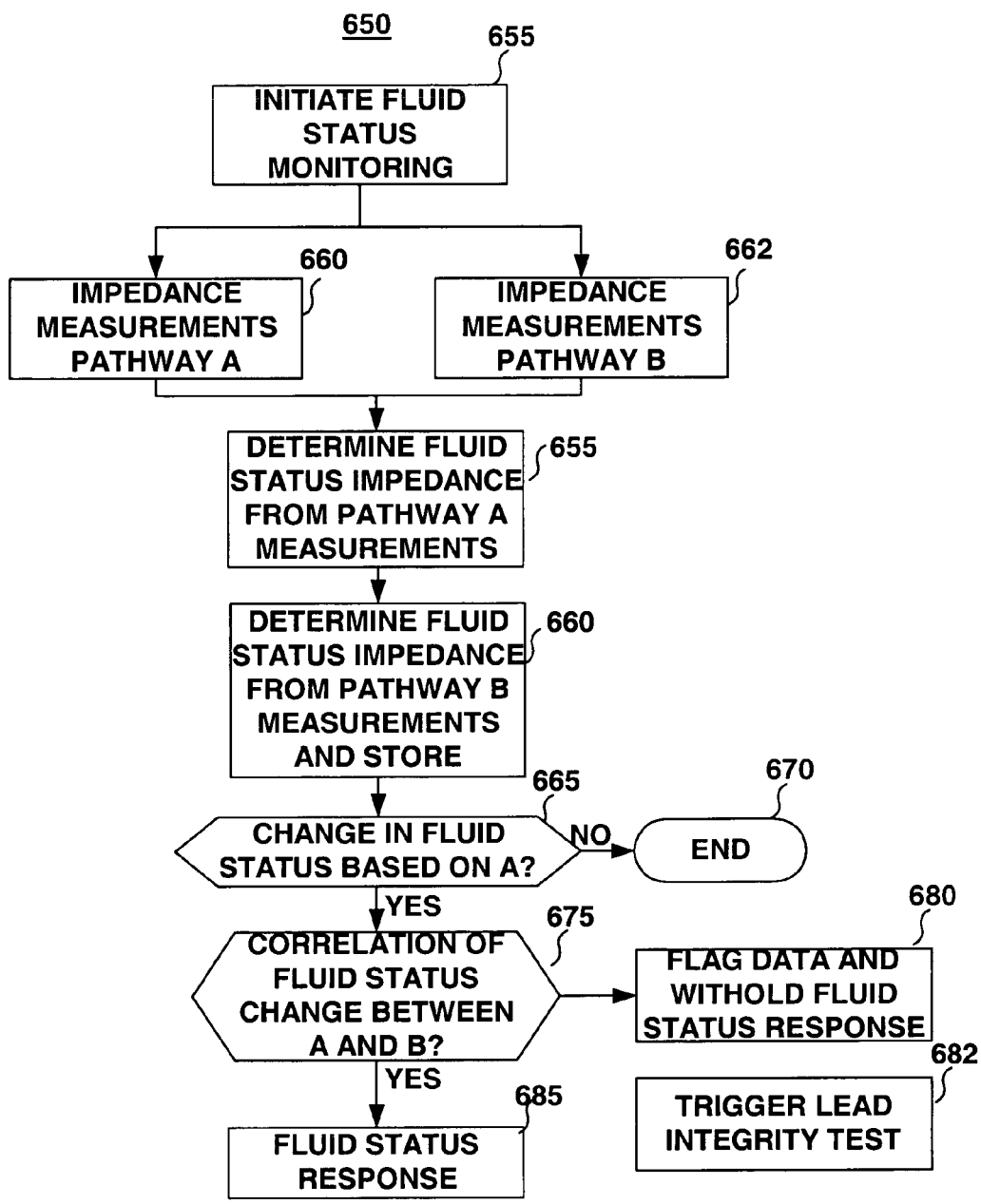
FIG. 12 is a flow chart of an alternative method for verifying fluid status monitoring results using a cross-check between different impedance measurement pathways.

FIG. 12 is a flow chart of an alternative method for verifying fluid status monitoring results using a cross-check between different impedance measurement pathways. Method 650 begins at step 655 when fluid status monitoring is initiated. Impedance measurements taken for deriving a fluid status impedance value are acquired from two different pathways A and B, as indicated by steps 660 and 662, during fluid status monitoring. Impedance measurements may be acquired from pathways A and B simultaneously, in an alternating fashion, or sequentially. Impedance measurements performed using measurement pathways A and B may use a common excitation pathway or exclusive excitation pathways. With regard to the ICD system shown in FIG. 1, a preferred measurement pathway A may be selected as the RV coil to can pathway, and measurement pathway B may be selected as the SVC coil to can or alternatively the CS coil to can. However, first and second impedance measurement pathways may be selected from any available electrodes included in the implanted system.

The implanted system with which the method shown in FIG. 11 may be used is also not limited to ICD systems. In cardiac stimulation systems having a set of leads which does not include high-voltage coil electrodes, such as a dual chamber pacemaker for example, first and second measurement pathways may be selected from the available pace/sense electrodes. For example, a first measurement pathway may be selected as a RV tip or ring electrode to can pathway and a second measurement pathway may be selected as a RA tip or ring electrode to can pathway.

At step 655, a fluid status parameter is determined from the primary measurement pathway A. At step 660, a second fluid status parameter is determined from the cross-check measurement pathway B. The second fluid status parameter is stored in memory at step 660.

At step 665, a determination is made whether a clinically-relevant change in fluid status has occurred based on the impedance measurements acquired from the primary measurement pathway A. If no change has occurred, method 650 is terminated at step 670. If, however, a clinically relevant change is tentatively diagnosed at step 665 based on pathway A measurements, a comparison is made between the fluid status parameters determined from pathway A impedance measurements and pathway B impedance measurements. If a high correlation exists between the fluid status parameters determined from pathway A and pathway B, the tentative diagnosis of a fluid status change is deemed valid, and a fluid status response may be generated at step 685.

However, if there is a low correlation between the fluid status parameters determined from pathway A and pathway B, the data is flagged at step 680 to draw the attention of a clinician upon the next data review. The fluid status response is withheld at step 680.

A correlation is determined at step 675 using at least two fluid status parameters determined at two different points in time from each measurement pathway, one point being the most recently determined parameter and one or more points determined at previous points in time. Preferably, a correlation is determined from more than two points in time, however, to conserve battery energy and microprocessing time, a cross-check fluid status parameter may be determined only on a sampled basis.

Therefore, the impedance measurements acquired from the cross-check pathway B may be performed on a less frequent basis than impedance measurements acquired from primary measurement pathway A. In one embodiment, both primary measurement pathway A and cross-check pathway B are utilized to determine initial baseline fluid status parameters corresponding to each pathway when fluid status monitoring is first programmed to be enabled and preferably at a time when the patient is known to be stable. There after, impedance measurements are acquired using primary pathway A during every fluid status monitoring session, but impedance measurements from cross-check pathway B are acquired only on a sampled basis which is less frequent than the measurements performed on pathway A.

One advantage of including a cross-check of impedance measurements is that false positive fluid status change diagnoses and false positive lead integrity failure diagnoses may be reduced. Based on an absence in correlation between fluid status parameters derived from two impedance measurement pathways, a lead integrity test may optionally be triggered at step 682. If a lead integrity failure is diagnosed, the previous tentative fluid status change diagnosis may be canceled. Likewise, when a lead integrity failure is tentatively diagnosed based on a significant change in a measured lead impedance, but correlation between fluid status parameters derived from two different measurement pathways supports a diagnosis of a change in fluid status, the lead integrity diagnosis may be improper.

Figure 13:
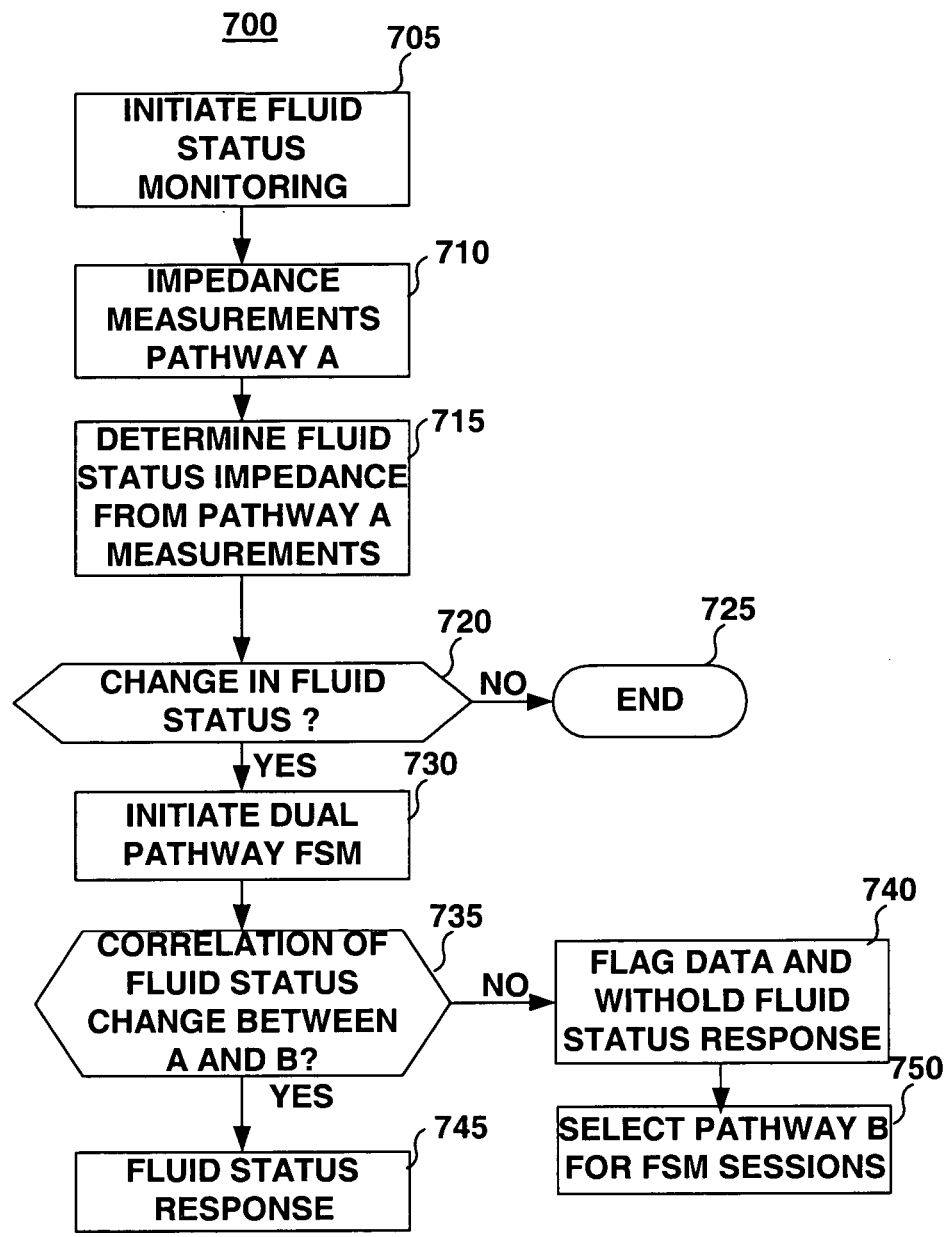
FIG. 13 is a flow chart of an alternative method for fluid status monitoring method that includes an impedance measurement cross-check.

FIG. 13 is a flow chart of an alternative method for fluid status monitoring method that includes an impedance measurement cross-check. In method 700, a primary impedance measurement pathway A is utilized for performing impedance measurements at step 710 after a fluid status monitoring session is initiated at step 705. If a change in fluid status is tentatively diagnosed at decision step 720, based on a fluid status impedance parameter determined from the pathway A impedance measurements at step 715, dual pathway fluid status monitoring is triggered at step 730. If there is no change in fluid status diagnosed based on pathway A impedance measurements, method 700 is terminated at step 725.

Dual pathway impedance measurements refers to the measurement of impedance along the primary pathway A and a cross-check pathway B, as described above, in a simultaneous, sequential or alternating manner. Dual pathway fluid status monitoring may be performed according to the original fluid status monitoring schedule. For example a series of impedance measurements may be performed on a daily basis and after a predetermined number of fluid status parameters have been determined for each pathway, for example after 2 to 10 days, a correlation analysis may be performed at step 735. If the fluid status trend for pathway B measurement does not correlate to a high degree with the trend derived from pathway A measurements, the tentative fluid change diagnosis is not supported. The related data may be flagged, and the fluid status response withheld at step 740, although a patient warning may still be generated to alert the patient to seek medical attention to evaluate the cause of the discordant results since the cause may be related to a lead integrity failure.

At step 750, an alternate measurement pathway, such as cross-check pathway B, may be selected for subsequent fluid status monitoring sessions to thereby eliminate aberrant results from pathway A. Alternatively, dual pathway fluid status monitoring may continue until reset by a clinician.

In alternative embodiments, dual pathway fluid status monitoring initiated at step 730 may be performed according to an accelerated fluid status monitoring schedule in order to quickly accumulate enough time points for performing correlation calculations between fluid status parameters derived from pathway A and B impedance measurements. Dual pathway fluid status monitoring may begin, for example, soon after a tentative fluid status change diagnosis is made rather than waiting for the next scheduled fluid status monitoring session, and impedance measurements may be made at more frequent intervals.

With regard to the preferred fluid status monitoring methods described herein, originally scheduled daily fluid monitoring sessions, scheduled to occur at a particular time of day, may include 16 measurement sets, encompassing 32 cardiac-gated impedance measurements each, scheduled 20 minutes apart. An accelerated schedule of dual pathway measurements may begin immediately upon a tentative fluid change diagnosis or at some predefined interval thereafter and include the same or a fewer number of measurement sets, for example 5 to 10 measurement sets, scheduled at the same or a shorter measurement set interval than originally scheduled.

By cross-checking impedance measurements when a fluid status change is tentatively diagnosed, impedance changes caused by physiological changes may be differentiated from impedance changes caused by physical changes in the lead systems. By tracking impedance measurements from two or more pathways, physiological changes that will affect all pathways presumably to a similar degree, such as tissue fluid content or blood resistivity, can be differentiated from lead-related impedance changes. Differentiation of physiological causes of impedance changes from lead-related causes of impedance changes will improve the specificity of both the physiological monitoring methods and the lead integrity monitoring methods.

The use of cross-check impedance measurements for differentiating lead-related and physiological causes of impedance changes may be beneficially employed in single-chamber, dual-chamber, or multi-chamber cardiac stimulation systems including at least three electrodes, one of which may be the can electrode, to allow testing of at least two distinct impedance measurement pathways. Impedance measurements may be performed using subthreshold impedance measurements as described herein or alternatively impedance measurements known for determining minute ventilation or any other impedance measurement method known in the art.

Many of the methods of the present invention may be embodied in executable instructions stored on a computer readable medium susceptible of being processed by myriad processor-based computing platforms. The present invention may thus be implemented on any of a wide variety of such computer readable media, all of which are expressly within the scope of the present invention. Of course, such processor-based computing platforms may be monolithic, networked and/or in wire line or wireless communication with other such platforms as is known and used in the field of computer operated systems and methods of processing.

While a detailed description of the preferred embodiments of the invention has been provided, it is recognized that numerous modifications or variations may be made to the methods and circuitry used in implementing cardiac-gated intra-thoracic impedance measurements for monitoring fluid tissue content as provided by the present invention. It is intended, therefore, in the following claims to cover all such changes and modifications as may fall within the true scope of the invention.

What is claimed is:

1. A method for monitoring intra-thoracic fluid content using an implanted cardiac stimulation device comprising at least two implanted electrodes, the method comprising:
   responsive to occurrence of a cardiac event, delivering an impedance measurement pulse at a predetermined interval therefrom;
   measuring impedance between the two electrodes using the delivered impedance measurement pulse;
   performing the first three steps repeatedly over a period extending over multiple days to acquire a set of impedance data;
   employing the set of impedance data to determine whether intra-thoracic fluid content is increasing or decreasing; and
   wherein the device comprises leads carrying the electrodes and wherein the method further comprises employing the measured impedances to assess the integrity of the leads.

2. A method for monitoring intra-thoracic fluid content using an implanted cardiac stimulation device comprising at least two implanted electrodes, the method comprising:
   responsive to occurrence of a cardiac event, delivering an impedance measurement pulse at a predetermined interval therefrom;
   measuring impedance between the two electrodes using the delivered impedance measurement pulse;
   performing the first three steps repeatedly over a period extending over multiple days to acquire a set of impedance data;
   employing the set of impedance data to determine whether intra-thoracic fluid content is increasing or decreasing;
   wherein the device comprises leads carrying the electrodes and wherein the method further comprises employing the measured impedances to assess the integrity of the leads and declaring the set of impedance data flawed responsive to the assessment of the integrity of the leads.

3. A method for monitoring intra-thoracic fluid content using an implanted cardiac stimulation device comprising at least two implanted electrodes, the method comprising:
   responsive to occurrence of a cardiac event, delivering an impedance measurement pulse at a predetermined interval therefrom;
   measuring impedance between the two electrodes using the delivered impedance measurement pulse;
   performing the first three steps repeatedly over a period extending over multiple days to acquire a set of impedance data;
   employing the set of impedance data to determine whether intra-thoracic fluid content is increasing or decreasing;
   wherein the device comprises leads carrying the electrodes and wherein the method further comprises employing the measured impedances to assess the integrity of the leads and wherein assessment of the integrity of the leads comprises comparing a measured impedance to a prior measured impedance to determine whether the measured impedance differs from the prior measured impedance by more than a defined amount.

4. A method for monitoring intra-thoracic fluid content using an implanted cardiac stimulation device comprising at least two implanted electrodes, the method comprising:
   responsive to occurrence of a cardiac event, delivering an impedance measurement pulse at a predetermined interval therefrom;
   measuring impedance between the two electrodes using the delivered impedance measurement pulse;
   performing the first three steps repeatedly over a period extending over multiple days to acquire a set of impedance data;
   employing the set of impedance data to determine whether intra-thoracic fluid content is increasing or decreasing; and
   declaring the set of impedance data flawed is performed responsive to a said measured impedance differing from a prior said measured impedance by more than a defined amount.

5. The method of claim 4, further comprising declaring the set of impedance data valid responsive to the said measured impedance differing from the said prior measured impedance by less than the defined amount.

6. A method for monitoring intra-thoracic fluid content using an implanted cardiac stimulation device comprising at least two implanted electrodes, the method comprising:
   responsive to occurrence of a cardiac event, delivering an impedance measurement pulse at a predetermined interval therefrom;
   measuring impedance between the two electrodes using the delivered impedance measurement pulse;
   performing the first three steps repeatedly over a period extending over multiple days to acquire a set of impedance data;
   employing the set of impedance data to determine whether intra-thoracic fluid content is increasing or decreasing; and
   wherein the device comprises at least a third electrode and wherein the method further comprises performing a cross check of the measured impedance values by measuring an impedance using the third electrode.

7. The method of claim 6, wherein the method further comprises declaring the set of impedance data flawed is performed responsive to the impedance measured using the third electrode.

8. An implantable device capable of measuring intra-thoracic fluid content, comprising:
- at least two implantable electrodes:
- means for determining occurrences of cardiac events;
- an impedance measurement means for measuring impedance between the electrodes repeatedly over a period extending over multiple days to acquire a set of impedance data, the impedance measurement means comprising:
  - means responsive to occurrence of a cardiac event, for delivering an impedance measurement pulse separated by a predetermined interval therefrom;
  - means for measuring impedance between the two electrodes using the delivered impedance measurement pulse; and
  - means responsive to the set of impedance data for determining whether intra-thoracic fluid content is increasing or decreasing; and
- wherein the device comprises leads carrying the electrodes and wherein the device further comprises means for employing the measured impedances to assess the integrity of the leads.

9. An implantable device capable of measuring intra-thoracic fluid content, comprising:
- at least two implantable electrodes:
- means for determining occurrences of cardiac events;
- an impedance measurement means for measuring impedance between the electrodes repeatedly over a period extending over multiple days to acquire a set of impedance data, the impedance measurement means comprising:
  - means responsive to occurrence of a cardiac event, for delivering an impedance measurement pulse separated by a predetermined interval therefrom;
  - means for measuring impedance between the two electrodes using the delivered impedance measurement pulse; and
  - means responsive to the set of impedance data for determining whether intra-thoracic fluid content is increasing or decreasing; and
- wherein the device comprises leads carrying the electrodes and wherein the device further comprises means for employing the measured impedances to assess the integrity of the leads; and
- further comprising means for declaring the set of impedance data flawed responsive to the assessment of the integrity of the leads.

10. An implantable device capable of measuring intra-thoracic fluid content, comprising:
- at least two implantable electrodes:
- means for determining occurrences of cardiac events;
- an impedance measurement means for measuring impedance between the electrodes repeatedly over a period extending over multiple days to acquire a set of impedance data, the impedance measurement means comprising:
  - means responsive to occurrence of a cardiac event, for delivering an impedance measurement pulse separated by a predetermined interval therefrom;
  - means for measuring impedance between the two electrodes using the delivered impedance measurement pulse; and
  - means responsive to the set of impedance data for determining whether intra-thoracic fluid content is increasing or decreasing; and
- wherein the device comprises leads carrying the electrodes and wherein the device further comprises means for employing the measured impedances to assess the integrity of the leads; and
- wherein the means for assessment of the integrity of the leads comprises means for comparing a measured impedance to a prior measured impedance to determine whether the measured impedance differs from the prior measured impedance by more than a defined amount.

11. An implantable device capable of measuring intra-thoracic fluid content, comprising:
- at least two implantable electrodes:
- means for determining occurrences of cardiac events;
- an impedance measurement means for measuring impedance between the electrodes repeatedly over a period extending over multiple days to acquire a set of impedance data, the impedance measurement means comprising:
  - means responsive to occurrence of a cardiac event, for delivering an impedance measurement pulse separated by a predetermined interval therefrom;
  - means for measuring impedance between the two electrodes using the delivered impedance measurement pulse; and
  - means responsive to the set of impedance data for determining whether intra-thoracic fluid content is increasing or decreasing; and
- further comprising means for declaring the set of impedance data valid responsive to a measured impedance differing from a prior measured impedance by less than a defined amount.

12. An implantable device capable of measuring intra-thoracic fluid content, comprising:
- at least two implantable electrodes:
- means for determining occurrences of cardiac events;
- an impedance measurement means for measuring impedance between the electrodes repeatedly over a period extending over multiple days to acquire a set of impedance data, the impedance measurement means comprising:
  - means responsive to occurrence of a cardiac event, for delivering an impedance measurement pulse separated by a predetermined interval therefrom;
  - means for measuring impedance between the two electrodes using the delivered impedance measurement pulse; and
  - means responsive to the set of impedance data for determining whether intra-thoracic fluid content is increasing or decreasing; and
- further comprising means for declaring the set of impedance data flawed responsive to a measured impedance differing from a prior measured impedance by more than a defined amount.

13. The device of claim 11, further comprising means for declaring the set of impedance data valid responsive to a measured impedance differing from a prior measured impedance by less than the defined amount.

14. An implantable device capable of measuring intra-thoracic fluid content, comprising:
- at least two implantable electrodes:
- means for determining occurrences of cardiac events;
- an impedance measurement means for measuring impedance between the electrodes repeatedly over a period extending over multiple days to acquire a set of impedance data, the impedance measurement means comprising:

means responsive to occurrence of a cardiac event, for delivering an impedance measurement pulse separated by a predetermined interval therefrom;

means for measuring impedance between the two electrodes using the delivered impedance measurement pulse; and means responsive to the set of impedance data for determining whether intra-thoracic fluid content is increasing or decreasing; and further comprising:

a third electrode;

means for measuring an impedance employing the third electrode and means for performing a cross check of the set of impedance data by measuring an impedance using the third electrode.

15. The device of claim 14, further comprising:

means for declaring the set of impedance data flawed responsive to the impedance measured using the third electrode.

\* \* \* \* \*